(12) United States Patent
Hansen et al.

(10) Patent No.: US 6,303,620 B1
(45) Date of Patent: *Oct. 16, 2001

(54) COMPOUNDS WITH GROWTH HORMONE RELEASING PROPERTIES

(75) Inventors: Thomas Kruse Hansen, Herlev; Michael Ankersen, Frederiksberg, both of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/306,151

(22) Filed: May 6, 1999

Related U.S. Application Data

(60) Provisional application No. 60/085,886, filed on May 18, 1998, and provisional application No. 60/091,947, filed on Jul. 7, 1998.

(30) Foreign Application Priority Data

May 11, 1998 (DK) .............................................. 1998 00636
Jul. 1, 1998 (DK) .............................................. 1998 00875

(51) Int. Cl.⁷ ..................... C07D 211/80; C07D 421/00; C07D 401/00; C07D 285/06; C07D 209/02; A61K 31/435; A61K 31/54

(52) U.S. Cl. ......................... 514/278; 546/199; 546/201; 546/202; 546/205; 546/209; 546/218; 546/187; 546/189; 546/195; 546/196; 546/197; 546/198; 546/200; 546/207; 546/208; 546/210; 546/212; 546/214; 548/127; 548/128; 548/205; 548/214; 548/253; 548/306.1; 548/467; 548/468; 514/211; 514/247; 514/315; 514/316; 514/317; 514/318; 514/320; 514/321; 514/322; 514/323; 514/324; 514/326; 514/330; 540/519; 540/524

(58) Field of Search ................... 546/17, 193, 187, 546/189, 199, 201, 202, 205, 209, 210, 195, 196, 197, 198, 200, 212, 214, 226; 548/127, 128, 205, 214, 253, 306.1, 467, 468; 540/519, 524; 514/211, 247, 315, 316, 317, 318, 320, 321, 322, 323, 324, 326, 330, 278

(56) References Cited

U.S. PATENT DOCUMENTS

| 5,492,916 | 2/1996 | Morriello et al. | 514/318 |
| 5,721,250 | 2/1998 | Morriello et al. | 514/318 |

FOREIGN PATENT DOCUMENTS

| 2 308 064 | 6/1997 | (GB) | 546/193 |
| WO 95/13069 | 5/1995 | (WO) | 546/193 |
| WO 96/35713 | 11/1996 | (WO) | 546/193 |
| WO 96/38471 | 12/1996 | (WO) | 546/193 |
| WO 97/36873 | 10/1997 | (WO) | 546/193 |
| WO 98/16527 | 4/1998 | (WO) | 546/193 |

Primary Examiner—Alan L. Rotman
Assistant Examiner—Raymond Covington

(57) ABSTRACT

Disclosed are 4,4-disubstituted and 3,3-disubstituted piperidine compounds of formula I

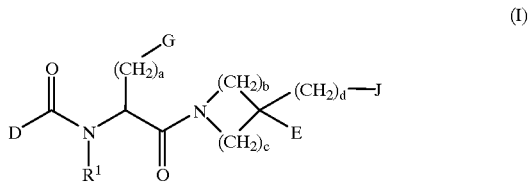

(I)

wherein D, E, G, J, R¹, a, b, c, and d are defined in the specification, compositions containing them, and their use for treating medical disorders resulting from a deficiency in growth hormone.

14 Claims, No Drawings

COMPOUNDS WITH GROWTH HORMONE RELEASING PROPERTIES

CROSS-REFERENCE TO RELATED APPLICATIONS

This application claims priority under 35 U.S.C. 119 of U.S. provisional application nos. 60/085,886 and 60/091,947 filed May 18, 1998 and Jul. 7, 1998, respectively, and Danish application nos. 1998 00636 and 1998 00875, filed May 11, 1998 and Jul. 1, 1998, respectively, the contents of which are fully incorporated herein by reference.

FIELD OF INVENTION

The present invention relates to novel compounds, in particular 4,4-disubstituted and 3,3-disubstituted piperidine compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 9517422, WO 9517423, WO 9514666, WO9419367, WO9534311, WO9602002, WO9615148, WO9613265, WO9622997, WO9635713, WO9638471, WO9632943, WO9700894, WO9706803, WO9709060, WO9707117, WO9711697, WO9722620, WO9723508, WO9724369, and WO9734604.

The composition of growth hormone releasing compounds is important for their growth hormone releasing potency as well as their bioavailability. It is therefore an object of the present invention to provide novel compounds with growth hormone releasing properties. Moreover, it is an object to provide novel growth hormone releasing compounds (growth hormone secretagogues) which are specific and/or selective and have no or substantially no side-effects, such as, e.g. release of LH, FSH, TSH, ACTH, vasopressin, oxytocin, cortisol and/or prolactin. It is also an object to provide compounds which have good oral bioavailability.

SUMMARY OF THE INVENTION

In accordance with the present invention there is provided novel compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase endogenous growth hormone release.

DESCRIPTION OF THE INVENTION

Accordingly, in a broad aspect the present invention relates to a compound of formula I

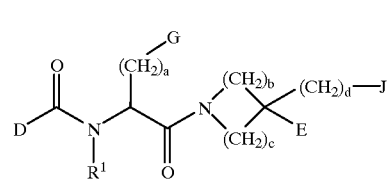

formula I wherein $R^1$ is hydrogen, or $C_{1-6}$-alkyl optionally substituted with one or more aryl or hetaryl;

a and d are independently of each other 0, 1, 2 or 3;

b and c are independently of each other 0, 1, 2, 3, 4 or 5, provided that b+c is 3, 4 or 5, D is

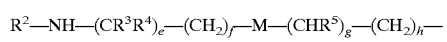

wherein $R^2$, $R^3$, $R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ may optionally form $-(CH_2)_i-U-(CH_2)_j-$, wherein i and j are independently 1 or 2 and U is $-O-$, $-S-$ or a valence bond;

h and f are independently 0, 1, 2, or 3;

g and e are independently 0 or 1;

M is a valence bond, $-CR^6=CR^7-$, arylene, hetarylene, $-O-$ or $-S-$;

$R^6$ and $R^7$ are independently hydrogen, or $C_{1-6}$alkyl optionally substituted with one or more aryl or hetaryl;

G is $-O-(CH_2)_k-R^8$,

-continued

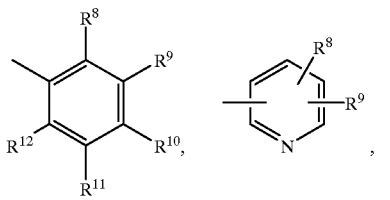

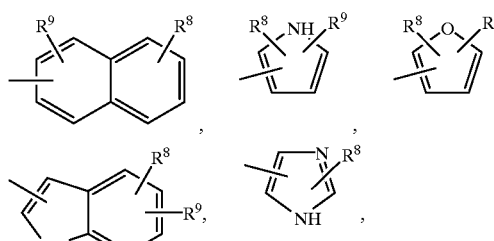

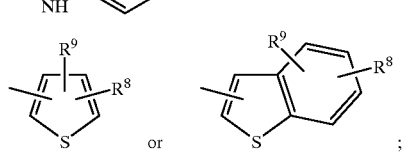

J is —O—(CH$_2$)$_l$—R$^{13}$,

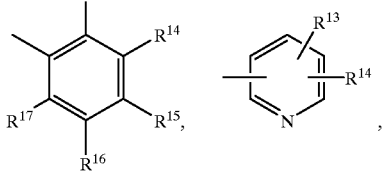

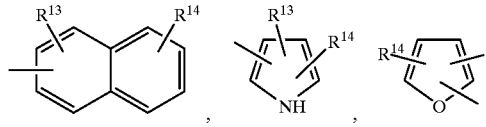

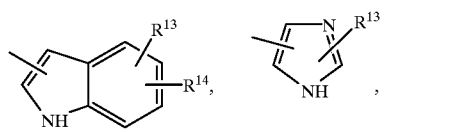

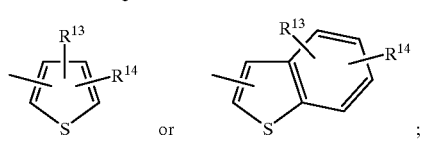

wherein R$^8$, R$^9$, R$^{10}$, R$^{11}$, R$^{12}$, R$^{13}$, R$^{14}$, R$^{15}$, R$^{16}$ and R$^{17}$ independently of each other are hydrogen, halogen, aryl, hetaryl, C$_{1-6}$-alkyl or C$_{1-6}$-alkoxy; k and l are independently 0, 1 or 2;

E is —CONR$^{18}$R$^{19}$, —COOR$^{19}$, —(CH$_2$)$_m$—NR$^{18}$SO$_2$R$^{20}$, —(CH$_2$)$_m$—NR$^{18}$COR$^{20}$, —(CH$_2$)$_m$—OR$^{19}$, —(CH$_2$)$_m$—OCOR$^{20}$, —CH(R$^{18}$)R$^{19}$, —(CH$_2$)$_m$—NR$^{18}$—CS—NR$^{19}$R$^{21}$ or —(CH$_2$)$_m$—NR$^{18}$—CO—NR$^{19}$R$^{21}$; or

E is —CONR$^{22}$NR$^{23}$R$^{24}$, wherein R$^{22}$ is hydrogen, C$_{1-6}$-alkyl optionally substituted with one or more aryl or hetaryl, or aryl or hetaryl optionally substituted with one or more C$_{1-6}$-alkyl; R$^{23}$ is C$_{1-6}$-alkyl optionally substituted with one or more aryl or hetaryl, or C$_{1-7}$-acyl; and R$^{24}$ is hydrogen, C$_{1-6}$-alkyl optionally substituted with one or more aryl or hetaryl; or aryl or hetaryl optionally substituted with one or more C$_{1-6}$-alkyl; or R$^{22}$ and R$^{23}$ together with the nitrogen atoms to which they are attached may form a heterocyclic system optionally substituted with one or more C$_{1-6}$-alkyl, halogen, amino, hydroxyl, aryl or hetaryl; or R$^{22}$ and R$^{24}$ together with the nitrogen atoms to which they are attached may form a heterocyclic system optionally substituted with one or more C$_{1-6}$-alkyl, halogen, amino, hydroxyl, aryl or hetaryl; or R$^{23}$ and R$^{24}$ together with the nitrogen atom to which they are attached may form a heterocyclic system optionally substituted with one or more C$_{1-6}$-alkyl, halogen, amino, hydroxyl, aryl or hetaryl;

wherein m is 0, 1, 2 or 3,

R$^{18}$, R$^{19}$ and R$^{20}$ independently are hydrogen or C$_{1-6}$-alkyl optionally substituted with halogen, —N(R$^{25}$)R$^{26}$, wherein R$^{25}$ and R$^{26}$ are independently hydrogen or C$_{1-6}$ alkyl; hydroxyl, C$_{1-6}$-alkoxy, C$_{1-6}$-alkoxycarbonyl, C$_{1-6}$-alkylcarbonyloxy or aryl;

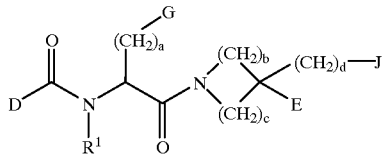

wherein

Q is —CH< or —N<,

K and L are independently —CH$_2$—, —CO—, —O—, —S—, —NR$^{27}$— or a valence bond, where R$^{27}$ is hydrogen or C$_{1-6}$ alkyl;

n and o are independently 0, 1, 2, 3 or 4;

R$^{20}$ is C$_{1-6}$ alkyl, aryl or hetaryl;

or a pharmaceutically acceptable salt thereof;

with the proviso that if M is a valence bond then E is —CONR$^{22}$NR$^{23}$R$^{24}$.

In a more narrow aspect the present invention relates to a compound of formula I formula I

wherein

R$^1$ is hydrogen, or C$_{1-6}$-alkyl optionally substituted with one or more aryl or hetaryl;

a and d are independently of each other 0, 1, 2 or 3;

b and c are independently of each other 0, 1, 2, 3, 4 or 5, provided that b+c is 3, 4 or 5, D is R$^2$—NH—(CR$^3$R$^4$)$_e$—(CH$_2$)$_f$—M—(CHR$^5$)$_g$—(CH$_2$)$_h$— wherein R$^2$, R$^3$, R$^4$ and R$^5$ are independently hydrogen or C$_{1-6}$ alkyl optionally substituted with one or more halogen, amino, hydroxyl, aryl or hetaryl; or R$^2$ and R$^3$ or R$^2$ and R$^4$ or R$^3$ and R$^4$ may optionally form —(CH$_2$)$_i$—U—(CH$_2$)$_j$—, wherein i and j are independently 1 or 2 and U is —O—, —S— or a valence bond;

h and f are independently 0, 1, 2, or 3;

g and e are independently 0 or 1;

M is —CR$^6$=CR$^7$—, arylene, hetarylene, —O— or —S—;

$R^6$ and $R^7$ are independently hydrogen, or $C_{1-6}$-alkyl optionally substituted with one or more aryl or hetaryl;

G is —O—$(CH_2)_k$—$R^8$,

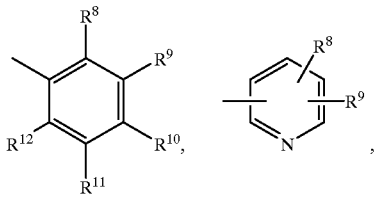

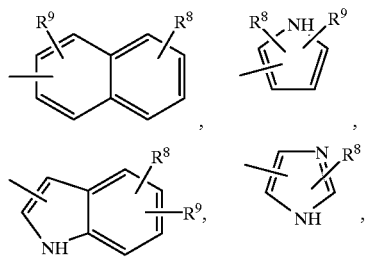

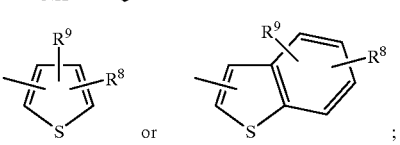

J is —O—$(CH_2)_l$—$R^{13}$,

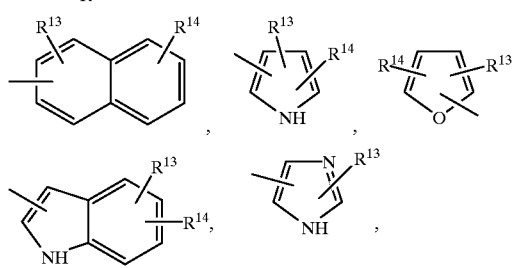

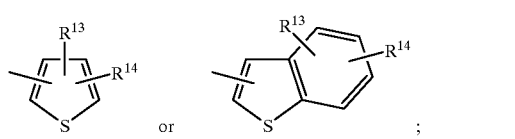

wherein $R^8$, $R^9$, $R^{10}$, $R^{11}$, $R^{12}$, $R^{13}$, $R^{14}$, $R^{15}$, $R^{16}$ and $R^{17}$ independently of each other are hydrogen, halogen, aryl, hetaryl, $C_{1-6}$alkyl or $C_{1-6}$-alkoxy;

k and l are independently 0, 1 or 2;

E is —$CONR^{18}R^{19}$, —$COOR^{19}$, —$(CH_2)_m$—$NR^{18}SO_2R^{20}$, —$(CH_2)_m$—$NR^{18}COR^{20}$, —$(CH_2)_m$—$OR^{19}$, —$(CH_2)_m$—$OCOR^{20}$, —$CH(R^{18})R^{19}$, —$(CH_2)_m$—$NR^{18}$—CS—$NR^{19}R^{21}$ or —$(CH_2)_m$—$NR^{18}$—CO—$NR^{19}R^{21}$; or

E is —$CONR^{22}NR^{23}R^{24}$, wherein $R^{22}$ is hydrogen, $C_{1-6}$-alkyl optionally substituted with one or more aryl or hetaryl, or aryl or hetaryl optionally substituted with one or more $C_{1-6}$-alkyl; $R^{23}$ is $C_{1-6}$alkyl optionally substituted with one or more aryl or hetaryl, or $C_{1-7}$-acyl; and $R^{24}$ is hydrogen, $C_{1-6}$alkyl optionally substituted with one or more aryl or hetaryl; or aryl or hetaryl optionally substituted with one or more $C_{1-6}$-alkyl; or $R^{22}$ and $R^{23}$ together with the nitrogen atoms to which they are attached may form a heterocyclic system optionally substituted with one or more $C_{1-6}$-alkyl, halogen, amino, hydroxyl, aryl or hetaryl; or $R^{22}$ and $R^{24}$ together with the nitrogen atoms to which they are attached may form a heterocyclic system optionally substituted with one or more $C_{1-6}$-alkyl, halogen, amino, hydroxyl, aryl or hetaryl; or $R^{23}$ and $R^{24}$ together with the nitrogen atom to which they are attached may form a heterocyclic system optionally substituted with one or more $C_{1-6}$-alkyl, halogen, amino, hydroxyl, aryl or hetaryl;

wherein m is 0, 1, 2 or 3, $R^{18}$, $R^{19}$ and $R^{21}$ independently are hydrogen or $C_{1-6}$-alkyl optionally substituted with halogen, —$N(R^{25})R^{26}$, wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl;

or $R^{19}$ is

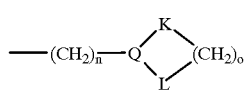

wherein

Q is —CH< or —N<,

K and L are independently —$CH_2$—, —CO—, —O—, —S—, —$NR^{27}$— or a valence bond, wherein $R^{27}$ is hydrogen or $C_{1-6}$ alkyl;

n and o are independently 0, 1, 2, 3 or 4;

$R^{20}$ is $C_{1-6}$ alkyl, aryl or hetaryl;

or a pharmaceutically acceptable salt thereof.

Moreover, the compounds of formula I may comprise any optical isomers thereof, in the form of separated, pure or partially purified optical isomers or racemic mixtures thereof. Whenever one or more chiral carbon atoms are present such chiral center or centers may be in the R- and/or S-configuration, or a mixture of R and S.

Furthermore, the compounds of formula I may have one or more carbon-carbon double bonds with the possibility of geometric isomers, and it is intended that possible stereoisomers (E or Z isomers) are included in the scope of the invention, unless a special geometric isomer is specified.

In one embodiment of the compound of formula I $R^1$ is hydrogen. In another embodiment of the compound of formula I $R^1$ is $C_{1-6}$-alkyl, such as $C_{1-4}$-alkyl, in particular methyl.

In a further embodiment of the compound of formula I a is 1.

In a still further embodiment of the compound of formula I d is 1.

In a further embodiment of the compound of formula I b is 1. In a still further embodiment of the compound of formula I b is 2. In a further embodiment of the compound of formula I b is 3.

In a still further embodiment of the compound of formula I c is 1. In a further embodiment of the compound of formula I c is 2. In a still further embodiment of the compound of formula I c is 3.

In a particular embodiment of the compound of formula I b+c is 4.

In a further embodiment of the compound of formula I D is $$R^2-NH-(CR^3R^4)_e-(CH_2)_f-M-(CHR^5)_g-(CH_2)_h-$$

wherein $R^2$, $R^3$, $R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ may optionally form —$(CH_2)_i$—U—$(CH_2)_j$—, wherein i and j are independently 1 or 2 and U is —O—, —S— or a valence bond, h and f are independently 0, 1, 2, or 3;

g and e are independently 0 or 1;

M is —$CR^6$=$CR^7$—, arylene, hetarylene, —O— or —S—; wherein $R^6$ and $R^7$ are independently hydrogen, or $C_{1-6}$-alkyl. In one embodiment $R^2$ is hydrogen. In a second embodiment $R^3$ is hydrogen. In a third embodiment $R^3$ is $C_{1-6}$ alkyl, in particular methyl. In a further embodiment $R^4$ is hydrogen. In a still further embodiment $R^4$ is $C_{1-6}$ alkyl, in particular methyl. In a further embodiment $R^3$ and $R^4$ form —$(CH_2)_i$—U—$(CH_2)_j$—. In a still further embodiment i is 1. In a further embodiment i is 2. In a still further embodiment j is 1. In a further embodiment j is 2. In a still further embodiment U is a valence bond. In a further embodiment $R^3$ and $R^4$ form —$(CH_2)_3$—. In a further embodiment h is 0. In a still further embodiment f is 0. In a further embodiment f is 1. In a further embodiment g is 0. In a still further embodiment e is 0. In a further embodiment e is 1. In a still further embodiment M is —$CR^6$=$CR^7$—, arylene, —O—, or —S—. In a further embodiment both of $R^6$ and $R^7$ are hydrogen or one of $R^6$ and $R^7$ is methyl and the other is hydrogen. In a still further embodiment M is the E-isomer of —$CR^6$=$CR^7$—. In a further embodiment M is —CH=CH—. In a still further embodiment M is —$C(CH_3)$=CH—. In a further embodiment M is arylene, in particular phenylene.

In a still further embodiment In a further embodiment of the compound of formula I D is $$R^2-NH-(CR^3R^4)_e-(CH_2)_f-M-(CHR^5)_g-(CH_2)_h-$$

wherein $R^2$, $R^3$, $R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ may optionally form —$(CH_2)_i$—$(CH_2)_j$—, wherein i and j are independently 1 or 2 and U is —O—, —S— or a valence bond, h and f are independently 0, 1, 2, or 3;

g and e are independently 0 or 1;

M is a valence bond. In one embodiment $R^2$ is hydrogen. In a second embodiment $R^3$ is hydrogen. In a third embodiment $R^3$ is $C_{1-6}$ alkyl, in particular methyl. In a further embodiment $R^4$ is hydrogen. In a still further embodiment $R^4$ is $C_{1-6}$ alkyl, in particular methyl. In a further embodiment $R^3$ and $R^4$ form —$(CH_2)_i$—U—$(CH_2)_j$—. In a still further embodiment i is 1. In a further embodiment i is 2. In a still further embodiment j is 1. In a further embodiment j is 2. In a still further embodiment U is a valence bond. In a further embodiment $R^3$ and $R^4$ form —$(CH_2)_3$—. In a further embodiment h is 0. In a still further embodiment f is 0. In a further embodiment f is 1. In a further embodiment g is 0. In a still further embodiment e is 0. In a further embodiment e is 1. In a preferred embodiment of the compound of formula I D is (1E)-4-amino-4-methylpent-1-enyl,
(1E)-4-amino-2,4-dimethylpent-1-enyl, (1E)-3-(1-aminocyclobutyl)prop-1-enyl, 1-amino-1-methylethyl, or 3-aminomethylphenyl.

In a still further embodiment of the compound of formula I G is —O—$(CH_2)_k$—$R^8$, wherein $R^8$, $R^9$, $R^{10}$, $R^{11}$ and $R^{12}$ independently of each other are hydrogen, halogen, aryl, hetaryl, $C_{1-6}$-alkyl or $C_{1-6}$-alkoxy; k is 0, 1 or 2. In a further embodiment $R^8$, $R^9$, $R^{10}$, $R^{11}$ and $R^{12}$ are independently of each other hydrogen. In a still further embodiment one of $R^8$, $R^9$, $R^{10}$, $R^{11}$ and $R^{12}$ is phenyl and the others are hydrogen, in particular $R^{10}$ is phenyl. In a further embodiment $R^8$ is phenyl. In a still further embodiment k is 1. In a still further embodiment G is phenyl, 1-naphthyl or 2-naphthyl, preferably phenyl or 2-naphthyl. In a further embodiment G is benzyloxy. In a still further embodiment G is 1H-indol. In a further embodiment G is biphenyl-4-yl.

In the above compound of formula I G is preferably 2-naphthyl, benzyloxy, 1H-indol or biphenyl-4-yl.

In a further embodiment of the compound of formula I J is wherein $R^{13}$, $R^{14}$, $R^{15}$, $R^{16}$ and $R^{17}$ independently of each other are hydrogen, halogen, aryl, hetaryl, $C_{1-6}$-alkyl or $C_{1-6}$-alkoxy. In a still further embodiment J is

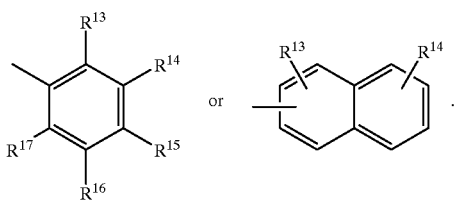

In a particular embodiment J is

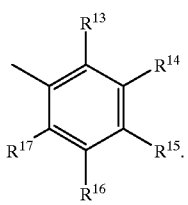

In a preferred embodiment $R^{13}$, $R^{14}$, $R^{15}$, $R^{16}$ and $R^{17}$ are all hydrogen.

In a still further embodiment of the compound of formula I E is —$CONR^{18}R^{19}$, —$COOR^{19}$ or —$(CH_2)_m$—$OR^{19}$, wherein m is 0, 1, 2 or 3, $R^{18}$ and $R^{19}$ independently are hydrogen or $C_{1-6}$-alkyl optionally substituted by halogen, —$N(R^{25})R^{26}$ wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl. In a particular embodiment E is —$CONR^{18}R^{19}$. In a further embodiment $R^{18}$ and $R^{19}$ are independently hydrogen or $C_{1-6}$-alkyl. In a particular embodiment one of $R^{18}$ and $R^{19}$ is hydrogen and the other is methyl. In a further embodiment E is —$COOR^{19}$. In a particular embodiment $R^{19}$ is $C_{1-6}$-alkyl, in particular ethyl.

In another embodiment E is —$CONR^{22}NR^{23}R^{24}$, wherein $R^{22}$ is hydrogen, $C_{1-6}$-alkyl optionally substituted with one or more aryl or hetaryl, or aryl or hetaryl optionally substituted with one or more $C_{1-6}$-alkyl; $R^{23}$ is $C_{1-6}$-alkyl optionally substituted with one or more aryl or hetaryl, or $C_{1-7}$-acyl; and $R^{24}$ is hydrogen, $C_{1-6}$-alkyl optionally substituted with one or more aryl or hetaryl; or aryl or hetaryl optionally substituted with one or more $C_{1-6}$-alkyl; or $R^{22}$ and $R^{23}$ together with the nitrogen atoms to which they are attached may form a heterocyclic system optionally substituted with one or more $C_{1-6}$-alkyl, halogen, amino, hydroxyl, aryl or hetaryl; or $R^{22}$ and $R^{24}$ together with the nitrogen atoms to which they are attached may form a heterocyclic system optionally substituted with one or more $C_{1-6}$-alkyl, halogen, amino, hydroxyl, aryl or hetaryl; or $R^{23}$ and $R^{24}$ together with the nitrogen atom to which they are attached may form a heterocyclic system optionally substituted with one or more $C_{1-6}$-alkyl, halogen, amino, hydroxyl, aryl or hetaryl. In a still further embodiment $R^{22}$ is hydrogen. In another embodiment $R^{22}$ is $C_{1-6}$-alkyl, such as $C_{1-4}$-alkyl, in particular methyl. In a further embodiment $R^{23}$ is $C_{1-6}$-alkyl, such as $C_{1-6}$-alkyl, in particular methyl. In another embodiment $R^{23}$ is $C_{1-7}$-acyl, such as $C_{2-4}$-acyl, in particular acetyl. In a still further embodiment of the compound of formula I $R^{24}$ is hydrogen. In another embodiment of the compound of formula I $R^{24}$ is $C_{1-6}$-alkyl, such as $C_{1-4}$-alkyl, in particular methyl. In a special embodiment $R^{22}$ is hydrogen and $R^{23}$ and $R^{24}$ are $C_{1-6}$-alkyl, such as $C_{1-4}$-alkyl, in particular methyl. In a further embodiment $R^{22}$ and $R^{23}$ may together with the nitrogen atoms to which they are attached form a heterocyclic system, which is optionally substituted with one or more $C_{1-6}$-alkyl, halogen, amino, hydroxyl, aryl or hetaryl. Such heterocyclic system, including $R^{22}$ and $R^{23}$, may be aromatic or non-aromatic and may be selected from e.g. pyrazole, pyridazine, triazine, indazole, phthalazine, cinnoline, pyrazolidine, or pyrazoline. In a still further embodiment $R^{22}$ and $R^{24}$ together with the nitrogen atoms to which they are attached form a heterocyclic system, which is optionally substituted with one or more $C_{1-6}$-alkyl, halogen, amino, hydroxyl, aryl or hetaryl. Such heterocyclic system, including $R^{22}$ and $R^{24}$, may be aromatic or non-aromatic and may be selected from e.g. pyrazole, pyridazine, triazine, indazole, phthalazine, cinnoline, pyrazolidine, or pyrazoline. In a further embodiment of the compound of formula I $R^{23}$ and $R^{24}$ together with the nitrogen atom to which they are attached form a heterocyclic system, which is optionally substituted with one or more $C_{1-6}$-alkyl, halogen, amino, hydroxyl, aryl or hetaryl. Such heterocyclic system, including $R^{22}$ and $R^{23}$, may be aromatic or non-aromatic and may be selected from e.g. aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine. In a particular embodiment $R^{23}$ and $R^{24}$ together with the nitrogen atom to which they are attached form pyrrolidine.

When $R^{22}$ and $R^{23}$ form a heterocyclic system $R^{23}$ and $R^{24}$ may simultaneously also form a heterocyclic system or $R^{24}$ may be hydrogen, $C_{1-6}$-alkyl optionally substituted with one or more aryl or hetaryl, or aryl or hetaryl optionally substituted with one or more $C_{1-6}$-alkyl.

When $R^{22}$ and $R^{24}$ form a heterocyclic system $R^{23}$ and $R^{24}$ may simultaneously also form a heterocyclic system or $R^{23}$ may be $C_{1-6}$-alkyl optionally substituted with one or more aryl or hetaryl, or $C_{1-7}$-acyl.

In the above compound of formula I E is preferably (methylamino)carbonyl, N,N-dimethylhydrazinocarbonyl, ethoxycarbonyl, or (pyrrolidin-1-yl)aminocarbonyl.

A particularly preferred group of compounds of formula I are such having formula Ia

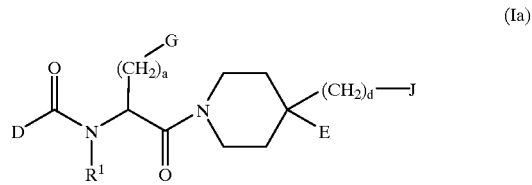

(Ia)

wherein $R^1$, D, G, E, J, a and d are as defined above.

Another particularly preferred group of compounds of formula I are such having formula Ib

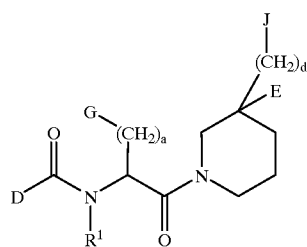

(Ib)

wherein R¹, D, G, E, J, a and d are as defined above.

Preferred compounds of formula I of the invention are:

1-{(2R)-2-[N-((2E)-5-Amino-5-methylhex-2-enoyl)-N-methylamino]-3-(2-naphthyl)propionyl}-4-benzylpiperidine-4-carboxylic acid methylamide

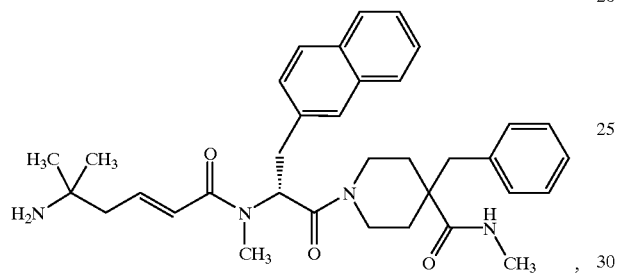

1-{(1R)-2-[N-((2E)-5-Amino-3,5-dimethylhex-2-enoyl)-N-methylamino]-3-(2-naphthyl)propionyl}-4-benzylpiperidine-4-carboxylic acid methylamide

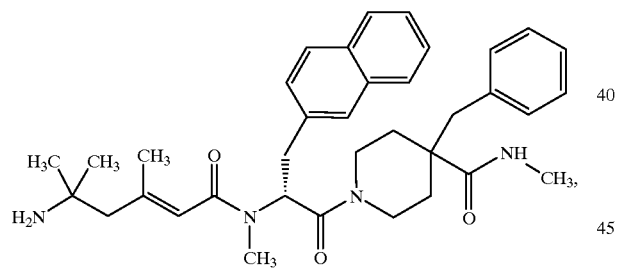

1-{(2R)-2-[N-((2E)-5-Amino-5-methylhex-2-enoyl)-N-methylamino]-3-(biphenyl-4-yl)propionyl}-4-benzylpiperidine-4-carboxylic acid methylamide

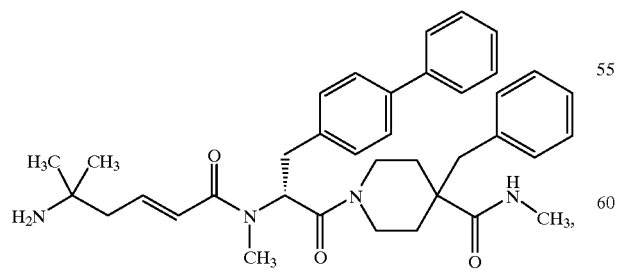

1-1R)-2-[N-((2E)-5-Amino-3,5-dimethylhex-2-enoyl)-N-methylamino]-3-(biphenyl-4-yl)propionyl)-4-benzylpiperidine-4-carboxylic acid methylamide

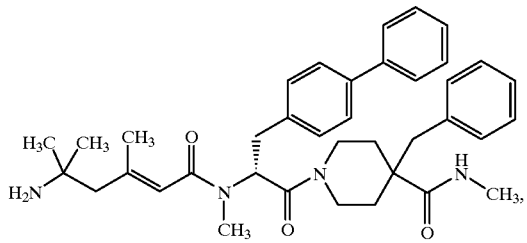

1-((2R)-2-{N-[(2E)4-(1-Aminocyclobutyl)but-2-enoyl]-N-methylamino}-3-(biphenyl-4-yl)propionyl)-4-benzylpiperidine-4-carboxylic acid methylamide

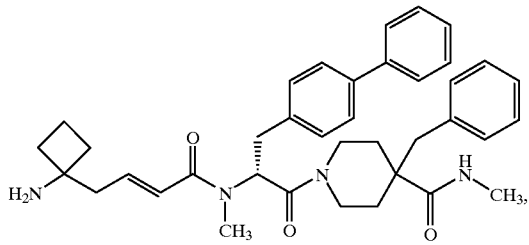

2-Amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide

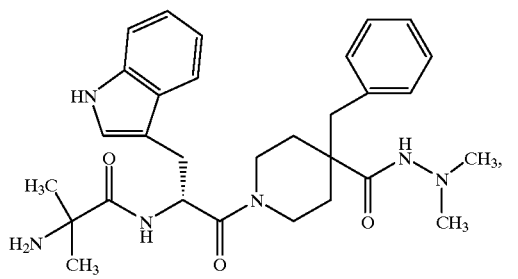

2-Amino-N-{(1R)-2-[(3R)-3-benzyl-3-(N',N'-dimethyl-hydrazinocarbonyl)-piperidin-1-yl]-1-benzyloxymethyl-2-oxo-ethyl}-2-methyl-propionamide

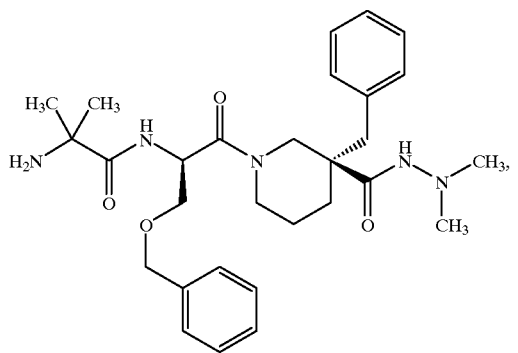

2-Amino-N-[(1R)-2-[(3R)-3-benzyl-3-(N'N'-dimethylhydrazinocarbonyl)-piperidin-1-yl]-1-((1H-indol-3-yl)methyl)-2-oxoethyl]-2-methylpropionamide

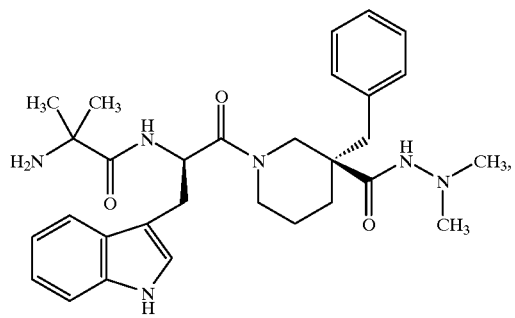

1-{(2R)-2-[N-((2E)-5-Amino-5-methylhex-2-enoyl)-N-methylamino]-3-(biphenyl-4-yl)propionyl}-4-benzylpiperidine-4-carboxylic acid ethyl ester

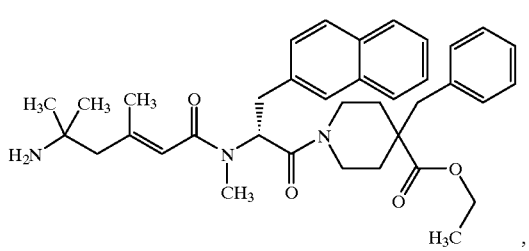

(3S)-1-[(2R)-2-((2E)-5-Amino-5-methylhex-2-enoylamino)-3-(1H-indol-3-yl)propionyl]-3-benzylpiperidine-3-carboxylic acid ethyl ester

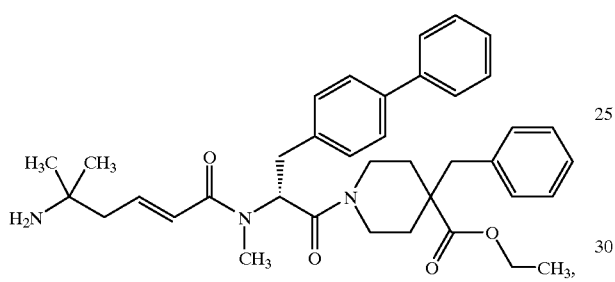

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid ethyl ester

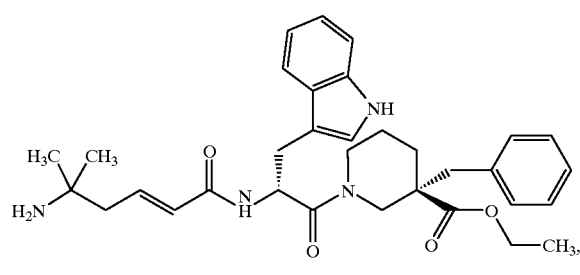

(3S)-1-[(2R)-2-((2E)-5-Amino-3,5-dimethylhex-2-enoylamino)-3-(1H-indol-3-yl)propionyl]-3-benzylpiperidine-3-carboxylic acid ethyl ester

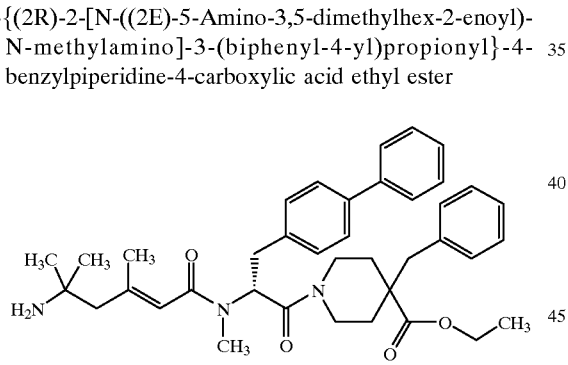

1-{(2R)-2-[N-((2E)-5-Amino-5-methylhex-2-enoyl)-N-methylamino]-3-(2-naphthyl)propionyl}-4-benzylpiperidine-4-carboxylic acid ethyl ester

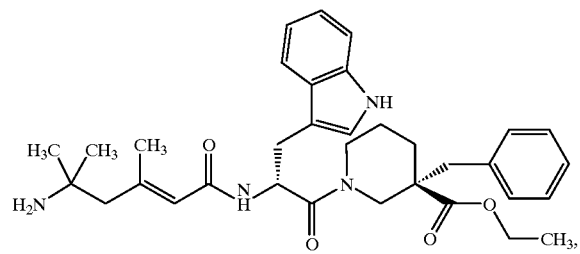

(3S)-1-[(2R)-2-(3-(Aminomethyl)benzoylamino)-3-(1H-indol-3-yl)propionyl]-3-benzylpiperidine-3-carboxylic acid ethyl ester

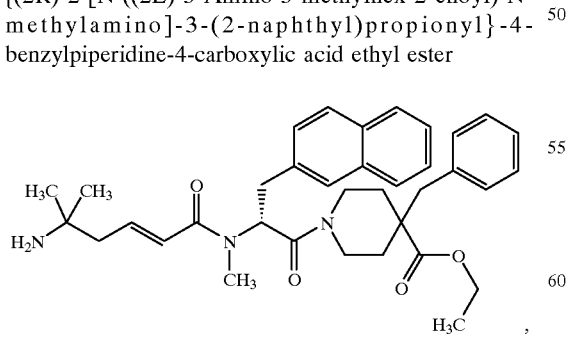

1-{(2R)-2-[N-((2E)-5-Amino-3,5-dimethylhex-2-enoyl)-N-methylamino]-3-(2-naphthyl)propionyl}-4-benzylpiperidine-4-carboxylic acid ethyl ester

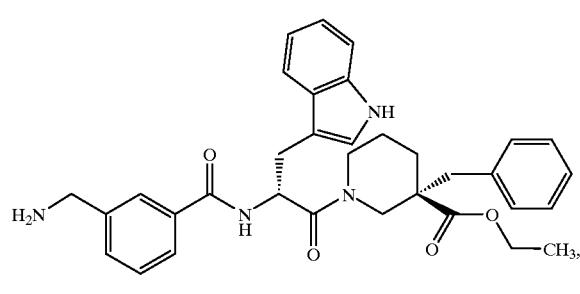

(2E)-5-Amino-5-methylhex-2-enoic acid N-{(1R)-2-[4-benzyl-4-(N',N'-dimethylhydrazinocarbonyl)piperidin-1-yl]-1-((2-naphthyl)methyl)-2-oxoethyl}-N-methylamide

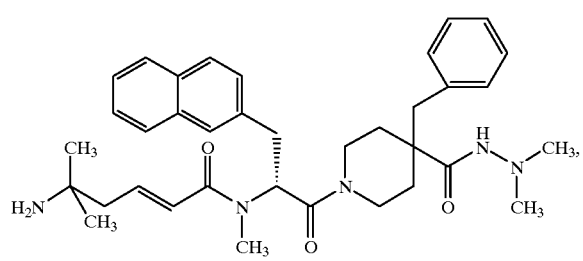

(2E)-5-Amino-5-methylhex-2-enoic acid N-[(1R)-2-[3-benzyl-3-(N',N'-dimethylhydrazinocarbonyl)-piperidin-1-yl]-1-((1H-indol-3-yl)methyl)-2-oxoethyl]amide

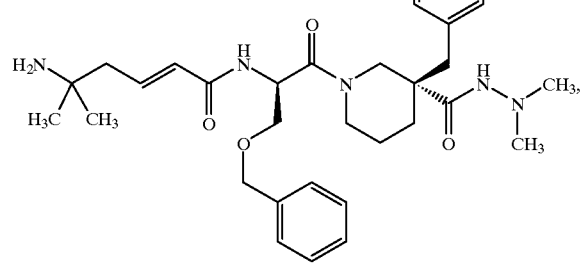

2-Amino-N-{2-[3-benzyl-3-(N',N'-dimethylhydrazinocarbonyl)piperidin-1-yl]-1-((2-naphthyl)methyl)-2-oxo-ethyl}-2-methyl-propionamide

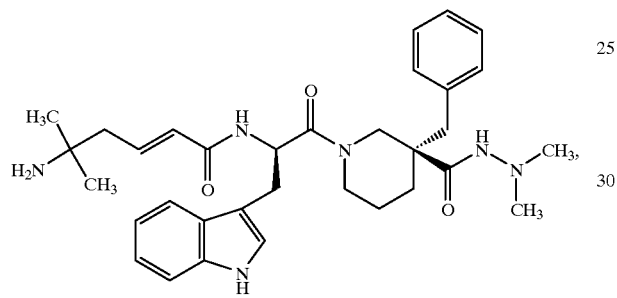

(2E)-5-Amino-5-methylhex-2-enoic acid N-{(1R)-2-[3-benzyl-3-(N',N'-dimethylhydrazinocarbonyl)-piperidin-1-yl]-1-((2-naphthyl)methyl)-2-oxoethyl}-N-methyl-amide

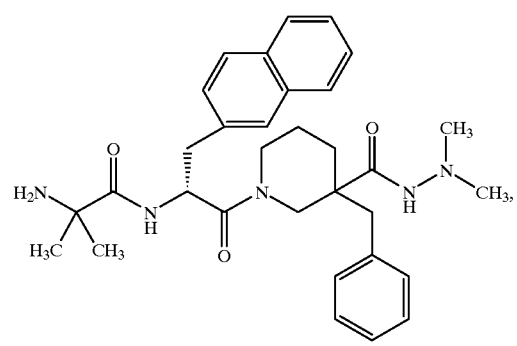

2-Amino-N-{(1R)-2-[3-benzyl-3-(N',N'-dimethylhydrazinocarbonyl)piperidin-1-yl]-1-((biphenyl-4-yl)methyl)-2-oxoethyl}-2-methylpropionamide

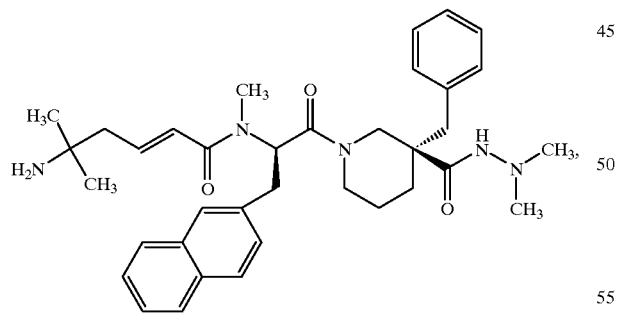

(2E)-5-Amino-5-methylhex-2-enoic acid {(1R)-2-[3-benzyl-3-(N',N'-dimethyl-hydrazinocarbonyl)piperidin-1-yl]-1-(benzyloxymethyl)-2-oxoethyl}amide

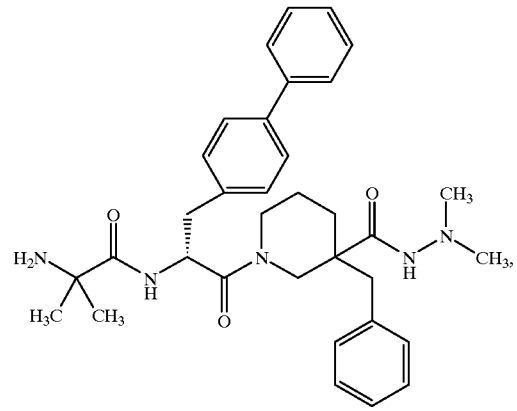

2-Amino-N-{(1R)-2-[3-benzyl-3-(N',N'-dimethylhydrazinocarbonyl)piperidin-1-yl]-1-((1H-indol-3-yl)methyl)-2-oxoethyl}-2-methylpropionamide

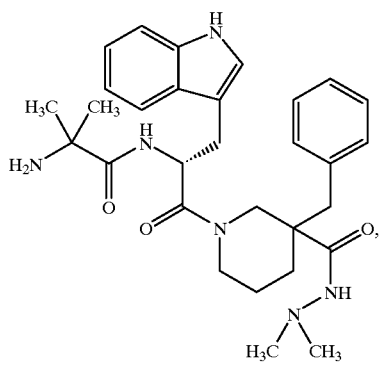

2-Amino-N-{2-[3-benzyl-3-(N'-dimethylhydrazinocarbonyl)piperidin-1-yl]-1-(benzyloxymethyl)-2-oxoethyl}-2-methylpropionamide

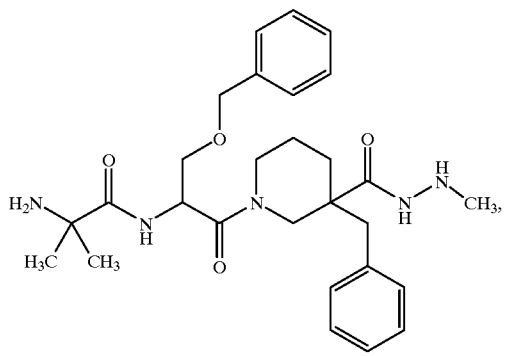

2-Amino-N-{(1R)-2-[3-benzyl-3-(N',N'-dimethylhydrazinocarbonyl)piperidin-1-yl]-1-(benzyloxymethyl)-2-oxoethyl}-2-methylpropionamide

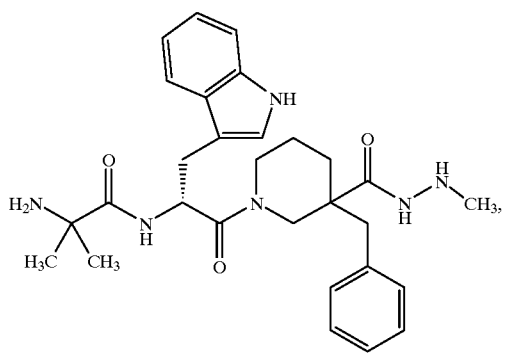

1-[(2R)-2-(2-Amino-2-methylpropionylamino)-3-(1-H-indol-3-yl)propionyl]-3-benzylpiperidine-3-carboxylic acid (pyrrolidin-1-yl)amide

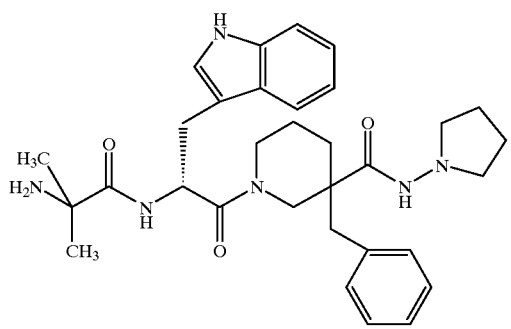

2-Amino-N-{(1R)-2-[3-benzyl-3-(N,N',N'-trimethylhydrazinocarbonyl)piperidin-1-yl]-1-((1H-indol-3yl)methyl)-2-oxoethyl}-2-methylpropionamide

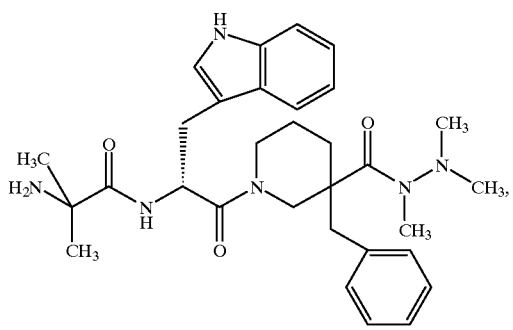

and pharmaceutically acceptable salts thereof.

GENERAL METHOD

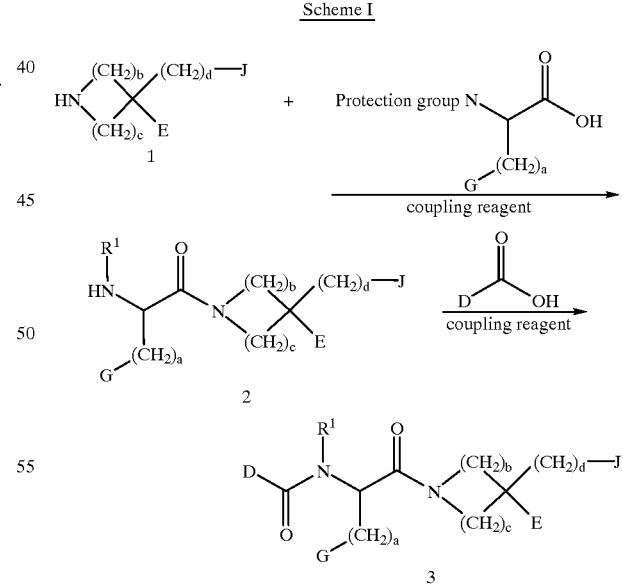

The procedures used in this patent and illustrated in above scheme I are based on peptide couplings well known in the art, and should in no way be interpreted as limiting the invention in any way. In the first step an amine (1) and a carboxylic acid is coupled to an amide by a coupling agent such as a carbodiimide and hydroxyazabenzoetriazole (HOAt). Prior to the next coupling a suitable protecting group such as tert butyloxycarbonyl (Boc) can be removed with methods well known to those skilled in the art, thereby producing compound (2). It is also possible to avoid the use of protecting groups. Hereafter (2) is coupled to a carboxylic acid of formula D—COOH by a coupling agent, thereby producing compound (3).

Scheme II

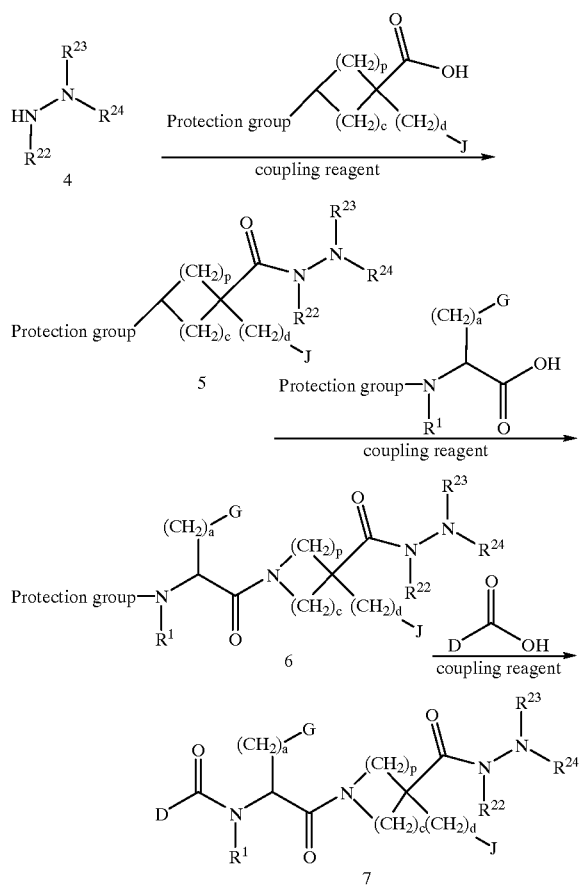

Compounds of the general structure I containing a hydrazine in the C-terminal may be prepared as illustrated above in scheme II. The procedures used in this patent and illustrated in above scheme II are based on peptide couplings well known in the art, and should in no way be interpreted as limiting the invention in any way. In the first step a mono-, di- or tri-substituted hydrazine or hydrazone (4) and an appropriate protected amino acid are coupled to form a compound (5) using a suitable coupling reagent such as 1-ethyl-3-(3-dimethylaminopropyl)carbodiimide hydrochloride, 1-hydroxybenzotriazole or another coupling reagent known in the art of peptide coupling in an appropriate solvent such as dimethylformamid or dichloromethane. Hereafter, the amide (5) and a carboxylic acid is coupled by a coupling agent, thereby producing compound (6). Hereafter (6) is coupled to a carboxylic acid of formula D—COOH by a coupling agent, thereby producing compound (7). In the procedure, prior to the next coupling a suitable protecting group such as tert butyloxycarbonyl (Boc) can be removed with methods well known to those skilled in the art. It is also possible to avoid the use of protecting groups. The appropriate amino acids may be protected and deprotected by methods known in the art and described by e.g. T. W. Green (Protective Groups in Organic Synthesis, 2. Ed., John Wiley and Sons, New York 1991).

The compounds of formula I exhibit an improved resistance to proteolytic degradation by enzymes because they are non-natural, in particular because the natural amide bonds are replaced by non-natural amide bond mimetics. The increased resistance to proteolytic degradation of the compounds of the invention in comparison with known hormone releasing peptides is expected to improve their bioavailability compared to that of the peptides suggested in the prior literature.

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$-cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

The $C_{1-7}$-acyl groups specified above are intended to include those acyl groups of the designated length in either a linear or branched or cyclic configuration. Examples of linear acyl are formyl, acetyl, propionyl, butyryl, valeryl, etc. Examples of branched are isobutyryl, isovaleryl, pivaloyl, etc. Examples of cyclic are cyclopentylcarbonyl, cyclohexylcarbonyl, etc.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$alkyl, $C_{1-6}$alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and naphthylene, optionally substituted with one or more $C_{1-6}$alkyl, $C_{1-6}$-alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$alkyl, $C_{1-6}$-alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted by one or more $C_1$-alkyl, $C_{1-6}$-alkoxy, halogen, amino or aryl.

In the present context, the term "heterocyclic system" is intended to include aromatic as well as non-aromatic ring moieties, which may be monocyclic, bicyclic or polycyclic, and contain in their ring structure at least one, such as one, two or three, nitrogen atom(s), and optionally one or more, such as one or two, other hetero atoms, e.g. sulpher or oxygen atoms. The heterocyclic system is preferably selected from pyrazole, pyridazine, triazine, indazole, phthalazine, cinnoline, pyrazolidine, pyrazoline, aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine.

The term "halogen" is intended to include chlorine (Cl), fluorine (F), bromine (Br) and iodine (I).

The compounds of the present invention may have one or more asymmetric centers (chiral carbon atoms) and it is intended that stereoisomers, as separated, pure or partially purified stereoisomers or racemic mixtures thereof are included in the scope of the invention.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, maleic, mandelic phthalic, citric, glutaric, gluconic, methanesulfonic, salicylic, succinic, tartaric, toluenesulfonic, trifluoracetic, sulfamic or fumaric acid and/or water.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, an effective amount of a compound of formula I or a pharmaceutically acceptable salt thereof, together with a pharmaceutically acceptable carrier or diluent.

Pharmaceutical compositions containing a compound of the present invention may be prepared by conventional techniques, e.g. as described in *Remington's Pharmaceutical Sciences*, 1985 or in *Remington: The Science and Practice of Pharmacy*, 19th Edition (1995). The compositions may appear in conventional forms, for example, capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.01–500 mg/day, e.g. from about 5 to about 50 mg, such as about 10 mg per dose, when administered to patients, e.g. humans, as a drug.

In a further aspect the present invention relates to a pharmaceutical composition in unit dose form, comprising as an active ingredient from about 10 to about 200 mg of the compound of formula I or a pharmaceutically acceptable salt thereof.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. Compounds of formula I are useful for stimulation of growth hormone release in the elderly; prevention of catabolic side effects of glucocorticoids, prevention and/or treatment of osteoporosis, treatment of chronic fatigue syndrome (CFS), treatment of acute fatigue syndrome and muscle loss following election surgery, stimulation of the immune system, acceleration of wound healing, accelerating bone fracture repair, accelerating complicated fractures, e.g. disctraction osteogenesis, treatment of wasting secondary to fractures, treatment of growth retardation, treating of growth retardation resulting from renal failure or insufficiency, treatment of cardiomyopathy, treatment of chronic liver disease, treatment of thrombocytopenia, treatment of Crohn's disease, treatment of short bowel syndrome, treatment of chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; increasing the growth rate of a patient having partial growth hormone insensitive syndrome, accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, treatment of cardiac failure or related vascular dysfunction, treatment of impaired cardiac function, treatment or prevention of myocardial infarction, lowering blood pressure, protection against ventricular dysfunction or prevention of reperfusion events, treatment of adults in chronic dialysis, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, treatment of sarcopenia, treatment of wasting in connection with AIDS, improvement in muscle strength, mobility, maintenance of skin thickness, metabolic homeostasis, renal homeostasis in the frail elderly, stimulation of osteoblasts, bone remodelling and cartilage growth, regulation of food intake, stimulation of the immune system in companion animals and treatment of disorder of aging in companion animals, promoting growth in livestock and stimulation of wool growth in sheep, treatment of metabolic syndrome (syndrome X), treatment of insulin resistance, including non-insulin dependent diabetes mellitus (NIDDM), in mammals, e.g. humans, improvement of sleep quality and correction of the relative hyposomatotropism of senescence due to high increase in REM sleep and a decrease in REM latency, and treatment of hypothermia. Treatment is also intended to include prophylactic treatment.

For the above indications the dosage will vary depending on the compound of formula I employed, on the mode of administration and on the therapy desired. Generally dosage levels between 0.0001 and 100 mg/kg body weight daily are administered to patients and animals to obtain effective release of endogenous growth hormone. Morever the compounds of formula I have no or substantially no side effects, when administered in the above dosage levels, such side effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula 1, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

PHARMACOLOGICAL METHODS

Compounds of formula I may be evaluated in vitro for their efficacy and potency to release growth hormone in rat pituitary primary cultures, and such evaluation may be performed as described below.

The isolation of rat pituitary cells is a modification of O. Sartor et al., *Endocrinology* 116, 1985, pp. 952–957. Male albino Sprague-Dawley rats (250+/–25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D-4902) pH 7.3, to a density of $2\times10^5$ cells/ml. The cells were seeded into microtiter plates (Nunc, Denmark), 200 ml/well, and cultured for 3 days at 37° C. and 8% $CO_2$.

COMPOUND TESTING

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability using the procedure described below:

Compounds is dissolved at a concentration of 1 mg/ml in water. 25 ml of this solution is added to 175 ml of the respective enzyme-solution (resulting in an enzyme-:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, MO, USA)

Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0.

Mass spectrometric analysis was performed using two different mass spectrometers. A Sciex API III triple quadru-pole LC-MS instrument (Sciex instruments, Thornhill, Ontario) equipped with an electrospray ion-source and a Bio-Ion 20 time-of-flight Plasma Desorption instrument (Biolon Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. Enzyme mix |
|---|---|---|---|
| Standards | | | |
| ACTH 4–10 | 1124.5/562.8 | + | − |
| Glucagon | 3483/871.8 | − | − |
| Insulin (B23–29) | 859.1/430.6 | | |
| Angiotensin 1–14 | 1760.1/881.0 | − | − |
| GHRP-2 | 817.4/409.6 | − | − |
| GHRP-6 | 872.6/437.4 | − | − |

+: Stable (less than 20% decrease in SIM signal after 24 h in degradation solution)
−: Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either High Performance Liquid Chromatography (HPLC), nuclear magnetic resonance (NMR, Bruker 400 MHz) or Liquid Chromatography-Mass Spectrometry (LC-MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se. The methanol/ammonia solution used is a 10% ammonia solution in methanol.

HPLC-Analysis:

Method A1.

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% acetonitrile in a buffer consisting of 0.1 M ammonium sulfate, which was adjusted to pH 2.5 with 4M sulfuric acid. after injection the sample was eluted by a gradient of 5% to 60% acetonitrile in the same buffer during 50 min.

Method B1.

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% (acetonitrile+0.1% TFA) in an aqueous solution of TFA in water (0.1%). After injection the sample was eluted by a gradient of 5% to 60% (acetonitrile+0.1% TFA) in the same aqueous buffer during 50 min.

LC-MS-Analysis:

The LC-MS analyses were performed on a PE Sciex API 100 LC/MS System using a Waters® 3 mm×150 mm 3.5 m C-18 Symmetry column and positive ionspray with a flow rate of 20 ml/min. The column was eluted with a linear gradient of 5–90% acetonitrile, 85–0% water and 10% trifluoroacetic acid (0.1%)/water in 15 min at a flow rate of 1 ml/min.

Abbrevations:
TLC: thin layer chromatography
DMSO: dimethylsulfoxide
min: minutes
h: hours
Boc: tert butyloxycarbonyl
DMF: dimethylformamide
THF: tetrahydrofuran
EDAC: N-ethyl-N'-dimethylaminopropylcarbodiimide hydrochloride
HOAt: 1-hydroxy-7-azabenzotriazole
DIEA: diisopropylethylamine
TFA: trifluoroacetic acid
Buildingblocks:

N-methylated aminoacids used in the following examples were prepared as in Can. J. Chem. 1977, 55, 906.

Example 1

1-{(2R)-2-[N-((2E)-5-Amino-5-methylhex-2-enoyl)-N-methylamino]-3-(2-naphthyl)propionyl}-4-benzylpiperidine-4-carboxylic acid methylamide Step A N-tert-butyloxycarbonyl-4-benzylpiperidine-4-carboxylic acid ethyl ester (prepared as in Gilligan et al J. Med. Chem. 1994, 364–370 using benzyl bromide as the alkylating agent) (11.0 g; 32 mmol) was refluxed for 7 h. in a mixture of ethanol (190 ml) and aqueous sodium hydroxide (18% 190 ml). The volume was reduced to a third in vacuo and pH was adjusted to 3 with sodium hydrogen sulfate. Water (300 ml) was added and the mixture was extracted with ethylacetate (2×250 ml). The combined organic phases were evaporated to afford 8.6 g of N-tert-butyloxycarbonyl-4-benzylpiperidine-4-carboxylic acid.

$^1$H-NMR: d (CDCl$_3$) 1.45 (s, 9H); 1.5 (m(br); 2H); 2.08 (m(br); 2H); 2.88 (m(br); 2H); 2.89 (s, 2H); 3.95 (m(br); 2H); 7.09–7.30 (5 arom. H).

Step B

4-Benzyl-4-methylcarbamoylpiperidine-1-carboxylic acid tert-butyl ester

N-tert-butyloxycarbonyl-4-benzylpiperidine-4-carboxylic acid (3.0 g; 9.0 mmol) was dissolved in methylene chloride (25 ml) and EDAC (1.8 g; 9.0 mmol) and HOAt (1.3 g; 9.0 mmol) was added. The mixture was stirred for 15 min, then methyl amine (33% in ethanol; 2.3 ml; 18 mmol) and DIEA (1.6 ml; 9.0 mmol) was added and the mixture was stirred overnight. Methylene chloride (100 ml) was added and the mixture was washed with a saturated aqueous solution of sodium hydrogen carbonate (50 ml) and a aqueous solution of sodium hydrogensulfate (10%, 50 ml), dried (MgSO$_4$) and evaporated in vacuo. The residue was chromatographed on silica (90 g) using a mixture of aqueous ammonia/ethanol/methylene chloride (1:7:92) as eluent to afford 2.8 g of 4-benzyl-4-methylcarbamoylpiperidine-1-carboxylic acid tert-butyl ester.

$^1$H-NMR: d (CDCl$_3$) 1.44 (s, 9H); 1.55 (m(br); 2H); 1.98 (m(br); 2H); 2.70 (d, 3H); 2.98 (m(br); 2H); 2.89 (s, 2H); 3.87 (m(br); 2H); 5.15 (q(br); 1H); 7.01–7.32 (5 arom. H).

Step C

4-Benzylpiperidine-4-carboxylic acid methylamide

4-Benzyl-4-methylcarbamoylpiperidine-1-carboxylic acid tert-butyl ester (2.8 g) was dissolved in a mixture of TFA and methylene chloride and stirred for 40 min. The solvent was removed in vacuo and the residue was dissolved in water (30 ml) and pH was adjusted to 13 with aqueous sodium hydroxide (1N). The aqueous phase was extracted with methylene chloride (3×75 ml) and the combined organic phases were dried (MgSO$_4$) and evaporated in vacuo to afford 1.50 g of 4-benzylpiperidine-4-carboxylic acid methylamide.

$^1$H-NMR: d (CDCl$_3$) 1.80 (td; 2H); 2.14 (d(br), 2H); 2.70 (d, 3H); 2.81 (s, 2H); 2.85 (dt; 2H); 3.21 (dt, 2H); 5.25 (t, 1H); 7.00–7.35 (5 arom. H).

Step D

4-Benzyl-1-((2R)-2-methylamino-3-(2-naphthyl)propionyl)piperidine-4-carboxylic acid methylamide (2R)-2-tert-Butyloxycarbonylamino-N-methyl-3-(2-naphthyl)propionic acid (709 mg; 2.15 mmol), HOAt (293 mg 2.25 mmol) and EDAC (412 mg; 2.25 mmol) were dissolved in methylene chloride (5 ml) and stirred for 15 min. 4-Benzylpiperidine-4-carboxylic acid methylamide (500 mg; 2.25 mmol) and DIEA (0.35 ml) were added and the mixture was stirred overnight. Methylene chloride (30 ml) was added and the mixture was washed with a saturated aqueous solution of sodium hydrogen carbonate (20 ml) and a aqueous solution of sodium hydrogensulfate (10%, 20 ml), dried (MgSO$_4$) and evaporated in vacuo. The residue was chromatographed on silica (40 g) using ethyl acetate as eluent to afford 810 mg of 4-benzyl-1-((2R)-2-(N-methyl-tert-butyloxycarbonylamino)-3-(2-naphthyl)propionyl) piperidine-4-carboxylic acid methylamide which was dissolved in TFA/methylene chloride (8+8 ml) and stirred for 40 min at RT. The solvent was removed in vacuo and the residue was neutralized with a saturated solution of sodium hydrogen carbonate and extracted with ethyl acetate (50 ml). The organic phase was dried (MgSO$_4$) and evaporated to afford 729 mg of 4-benzyl-1-((2R)-2-methylamino-3-(2-naphthyl)propionyl)piperidine-4-carboxylic acid methylamide.

Step E

4-Benzyl-1-((2R)-2-methylamino-3-(2-naphthyl)propionyl)piperidine-4-carboxylic acid methylamide (360 mg; 0.82 mmole) was coupled to (2E)-5-(tert-butyloxycarbonylamino)-5-methyl-2-hexenoic acid using the same coupling procedure as in step D. Removal of the N-terminal Boc group was performed as in step D but at −10° C. The crude product was purified on a RP-18-Seppak® (5 g; Waters) using a gradient from 0.1% TFA in water/acetonitrile 100/0 to 0.1% TFA in 60/40 water/acetonitrile to afford 306 mg of the title compound as a trifluoroacetate.

$^1$H-NMR: δ (MeOH) (selected peaks for major rotamer) 1.30 (s, 3H); 1.31 (a, 3H); 2.10 (AB-syst, 2H); 2.55 (s, 3H); 5.81 (m, 1H).
HPLC:
$r_t$=31.88 min(A1)
$r_t$=33.30 (B1)
ESMS: m/z: 569.4 (M+H)$^+$.

Example 2

1-{(1R)-2-[N-((2E)-5-Amino-3,5-dimethylhex-2-enoyl)-N-methylamino]-3-(2-naphthyl)propionyl}-4-benzylpiperidine-4-carboxylic acid methylamide

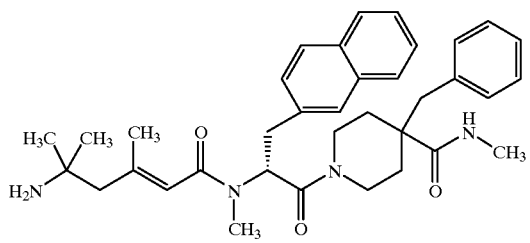

The compound was prepared as in example 1 using (2E)-5-(tert-butyloxycarbonylamino)-5,3-dimethyl-2-hexenoic acid instead of (2E)-5-(tert-butyloxycarbonylamino)-5-methyl-2-hexenoic acid in step E.
HPLC:
$r_t$=33.70 min(A1)
$r_t$=34.22 (B1)
ESMS: m/z: 583.4 (M+H)$^+$.

Example 3

1-{(2R)-2-[N-((2E)-5-Amino-5-methylhex-2-enoyl)-N-methylamino]-3-(biphenyl-4-yl)propionyl}-4-benzylpiperidine-4-carboxylic acid methylamide

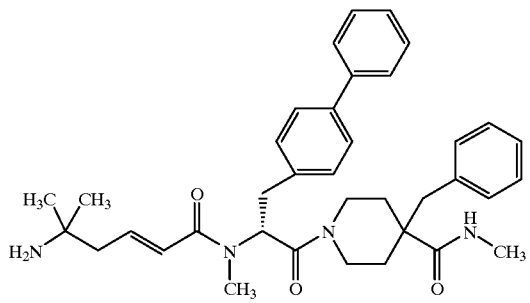

This compound was prepared as in example 1 using (2R)-2-tert-Butyloxycarbonylamino-N-methyl-3-(4-biphenylyl)propionic acid instead of (2R)-2-tert-Butyloxycarbonylamino-N-methyl-3-(2-naphthyl)propionic acid in step D.
HPLC:
$r_t$=34.53 min(A1)
$r_t$=36.15 (B1)
ESMS: m/z: 595.4 (M+H)$^+$.

Example 4

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid methylamide

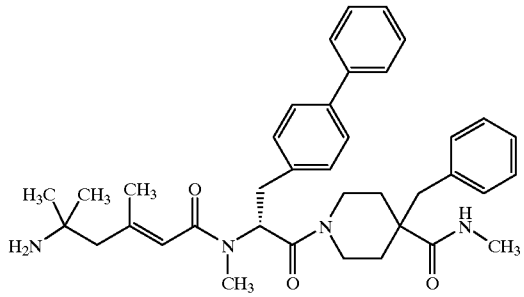

This compound was prepared as in example 1 using (2R)-2-tert-Butyloxycarbonylamino-N-methyl-3-(4-biphenylyl)propionic acid instead of (2R)-2-tert-Butyloxycarbonylamino-N-methyl-3-(2-naphthyl)propionic acid in step D and using (2E)-5-(tert-butyloxycarbonylamino)-5,3-dimethyl-2-hexenoic acid instead of (2E)-5-(tert-butyloxycarbonylamino)-5-methyl-2-hexenoic acid in step E.
HPLC:
$r_t$=35.15 min(A1)
$r_t$=36.83 (B1)
ESMS: m/z: 609.4 (M+H)$^+$.

Example 5

1-((2R)-2-{N-[(2E)-4-(1-Aminocyclobutyl)but-2-enoyl]-N-methylamino}-3-(biphenyl-4-yl)propionyl)-4-benzylpiperidine-4-carboxylic acid methylamide

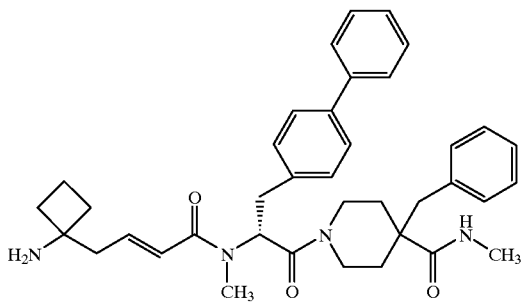

This compound was prepared as in example 1 using (2R)-2-tert-Butyloxycarbonylamino-N-methyl-3-(4-biphenylyl)propionic acid instead of (2R)-2-tert-Butyloxycarbonylamino-N-methyl-3-(2-naphthyl)propionic acid in step D and using (2E)-4-(1-(tert-butyloxycarbonylamino)cyclobutyl)but-2-enoic acid instead of (2E)-5-(tert-butyloxycarbonylamino)-5-methyl-2-hexenoic acid in step E.

HPLC: r$_t$=35.15 min (A1)
r$_t$=36.68 min (B1)
ESMS: m/z: 607.4 (M+H)$^+$.

Example 6

2-Amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide

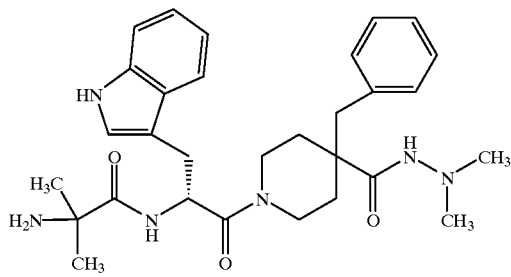

4-Benzyl-4-(N',N'-dimethylhydrazinocarbonyl)piperidine-1-carboxylic acid tert-butyl ester

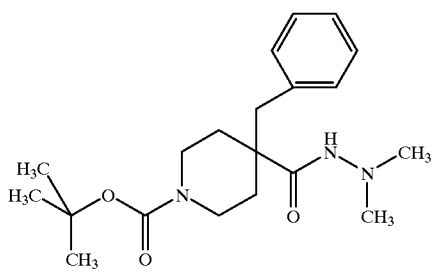

To a solution of 4-benzylpiperidine-1,4-dicarboxylic acid 1-tert-butyl ester (0.75 g, 2.35 mmol) (prepared as in Gilligan et al J. Med. Chem. 1994, 364–370) in methylene chloride (10 ml) was added 1-hydroxy-7-azabenzotriazole (0.32 mg, 2.35 mmol) and 1-ethyl-3-(3-dimethylaminopropyl)carbodiimide hydrochloride (0.45 g, 2.35 mmol) and the mixture was stirred for 30 min. Then N',N'-dimethylhydrazine (0.27 ml, 3.53 mmol) and diisopropylethylamine (0.52 ml, 3.06 mmol) was added and the mixture was stirred for 2 days. Methylene chloride (100 ml) was added and the mixture was washed with saturated aqueous sodium hydrogencarbonate (20 ml), water (20 ml), dried (MgSO$_4$), filtered and concentrated in vacuo. The obtained oil was chromatographed on silica (40 g) with heptane/ethyl acetate (1:2) to give 0.76 g of 4-benzyl-4-(N',N'-dimethylhydrazinocarbonyl)piperidine-1-carboxylic acid tert-butyl ester as a colorless oil.

HPLC: R$_t$=9.66 min (H8)
LC-MS: R$_t$=9.29 min, m/z=362.0 (m+1).

4-Benzylpiperidine-4-carboxylic acid N,N'-dimethylhydrazide

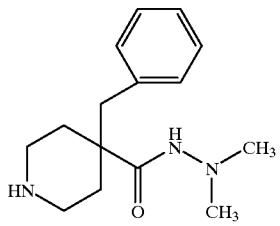

To a solution of 4-benzyl-4-(N',N'-dimethylhydrazinocarbonyl)piperidine-1-carboxylic acid tert-butyl ester (0.76 g, 2.02 mmol) in methylene chloride (2 ml) at 0° C. was added trifluoroacetic acid (5 ml) and the mixture was stirred for 60 min. The mixture was quenched with ethanol (20 ml), concentrated in vacuo and stripped three times with methylene chloride to give 4-benzylpiperidine-4-carboxylic acid N',N'-dimethylhydrazide in quantitative yield.

LC-MS: R$_t$=5.64 min, m/z=262.0 (m+1).

(2-(4-Benzyl-4-(N',N'-dimethylhydrazinocarbonyl)piperidine-1-yl)-1-(1H-indole-3-ylmethyl)-2-oxoethyl)carbamic acid tert-butyl ester

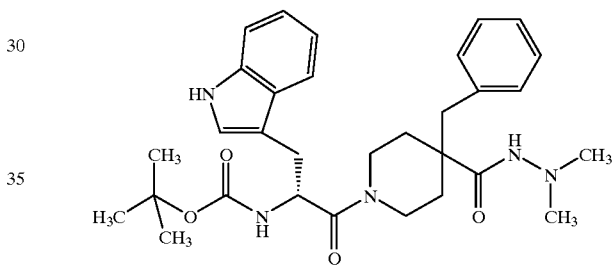

To a solution of 2-tert-butoxycarbonylamino-3-(1H-indole-3-yl)propionic acid (0.37 g, 1.2 mmol) in methylene chloride (15 ml) and dimethylformamid (5 ml) was added 1-hydroxy-7-azabenzotriazole (0.16 mg, 1.20 mmol) and 1-ethyl-3-(3-dimethylaminopropyl)carbodiimide hydrochloride (0.23 9, 1.20 mmol) and the mixture was stirred for 30 min. Then 4-benzylpiperidine-4-carboxylic acid N',N'-dimethylhydrazide (0.26g, 1.0 mmol) and diisopropylethylamine (0.69 ml, 4.0 mmol) was added and the mixture was stirred overnight. Methylene chloride (100 ml) was added and the mixture was washed with saturated aqueous sodium hydrogencarbonate (20 ml), water (20 ml), dried (MgSO$_4$), filtered and concentrated in vacuo. The obtained oil was chromatographed on silica (40 g) with methylene chloride/ (10% ammonia in methanol) (9:1) to give 0.43 g of (2-(4-benzyl-4-(N',N'-dimethylhydrazinocarbonyl)piperidine-1-yl)-1-(1H-indole-3-ylmethyl)-2-oxoethyl)carbamic acid tert-butyl ester as a colorless oil.

HPLC: R$_t$=10.45 min (H8)
LC-MS: R$_t$=9.92 min, m/z=548.2 (m+1).

1-(2-Amino-3-(1H-indol-3-yl)propionyl)-4-benzylpiperidine-4-carboxylic acid N',N'-dimethylhydrazide

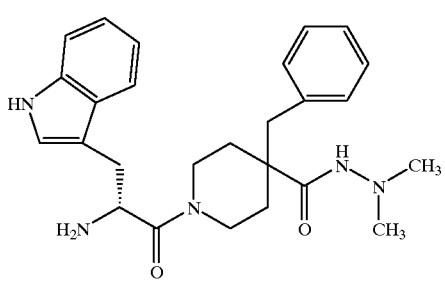

To a solution of (2-(4-benzyl-4-(N',N'-dimethylhydrazinocarbonyl)piperidine-1-yl)-1-(1H-indole-3-ylmethyl)-2-oxoethyl)carbamic acid tert-butyl ester (0.40 g, 0.73 mmol) in methylene chloride (3 ml) at 0° C. was added trifluoroacetic acid (3 ml) and the mixture was stirred for 30 min. The mixture was quenched with ethanol (20 ml), concentrated in vacuo and stripped three times with methylene chloride to give 0.63 g of 1-(2-amino-3-(1H-indol-3-yl)propionyl)-4-benzylpiperidine-4-carboxylic acid N',N'-dimethylhydrazide as a colorless oil.

HPLC: $R_t$=7.52 min (H8)

LC-MS: $R_t$=7.61 min, m/z=448.4 (m+1).

(1-(2-(4-Benzyl-4-(N',N'-dimethylhydrazinocarbonyl)piperidine-1-yl)-1-(1H-indol-3-ylmethyl)-2-oxoethylcarbamoyl)-1-methylethyl)carbamic acid tert-butyl ester

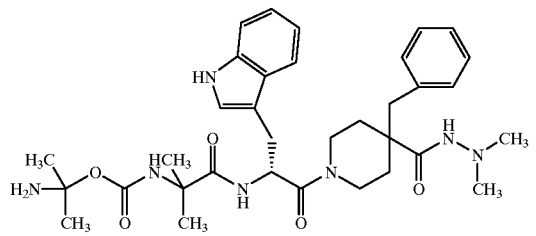

To a solution of 2-tert-butoxycarbonylamino-2-methylpropionic acid (0.18 g, 0.88 mmol) in methylene chloride (10 ml) was added 1-hydroxy-7-azabenzotriazole (0.12 mg, 0.88 mmol) and 1-ethyl-3-(3-dimethylaminopropyl)carbodiimide hydrochloride (0.12 g, 0.88 mmol) and the mixture was stirred for 30 min. Then 1-(2-amino-3-(1H-indol-3-yl)propionyl)-4-benzylpiperidine-4-carboxylic acid N',N'-dimethylhydrazide (0.46 g, 0.73 mmol) and diisopropylethylamine (0.50 ml, 2.92 mmol) was added and the mixture was stirred overnight. Methylene chloride (100 ml) was added and the mixture was washed with saturated aqueous sodium hydrogencarbonate (20 ml), water (20 ml), dried ($MgSO_4$), filtered and concentrated in vacuo. The obtained oil was chromatographed on silica (40 g) with methylene chloride/(10% ammonia in methanol) (9:1) to give 0.31 g of (1-(2-(4-benzyl-4-(N',N'-dimethylhydrazinocarbonyl)piperidine-1-yl)-1-(1H-indol-3-ylmethyl)-2-oxoethylcarbamoyl)-1-methylethyl)carbamic acid tert-butyl ester as a colorless oil.

HPLC: $R_t$=10.25 min (H8)

LC-MS: $R_t$=9.66 min, m/z=633.2 (m+1).

2-Amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide

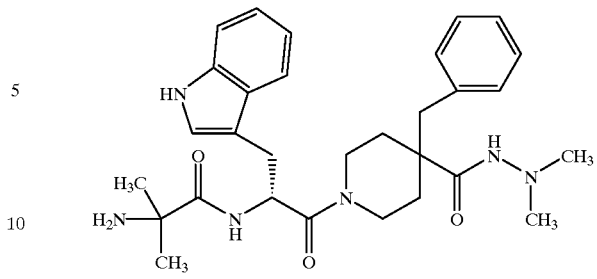

To a solution of (1-(2-(4-benzyl-4-(N',N'-dimethylhydrazinocarbonyl)piperidine-1-yl)-1-(1H-indol-3-ylmethyl)-2-oxoethylcarbamoyl)-1-methylethyl)carbamic acid tert-butyl ester (0.29 g, 0.46 mmol) in methylene chloride (3 ml) at 0° C. was added trifluoroacetic acid (3 ml) and the mixture was stirred for 30 min. The mixture was quenched with ethanol (20 ml), concentrated in vacuo and stripped three times with methylene chloride to give 0.25 g of 2-amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide as a white amorphous powder.

HPLC: $R_t$=24.56 min (A1), $R_t$=24.95 min (B1), $R_t$=7.73 min (H8)

LC-MS: $R_t$=7.74 min, m/z=533.4 (m+1).

Example 7

2-Amino-N-{(1R)-2-[(3R)-3-benzyl-3-(N',N'-dimethyl-hydrazinocarbonyl)-piperidin-1-yl]-1-benzyloxymethyl-2-oxo-ethyl}-2-methyl-propionamide

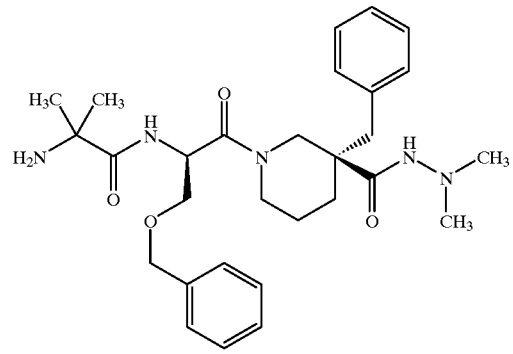

This compound was prepared using the procedure in example 6.

ESMS: m/z: 524.4 (M+H)$^+$.

Example 8

2-Amino-N-[(1R)-2-[(3R)-3-benzyl-3-(N'N'-dimethylhydrazinocarbonyl)-piperidin-1-yl]-1-(1H-indol-3-yl)methyl)-2-oxoethyl]-2-methylpropionamide

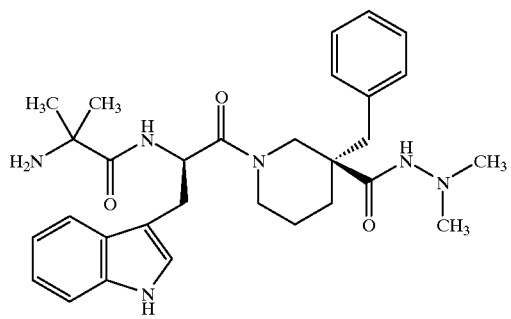

This compound was prepared using the procedure in example 6.

ESMS: m/z: 533.4 (M+H)+
HPLC: r$_t$: 27.60 min (A1)
HPLC: r$_t$: 26.84 min (B1).

Example 9

1-{(2R)-2-[N-((2E)-5-Amino-5-methylhex-2-enoyl)-N-methylamino]-3-(biphenyl-4-yl)propionyl}-4-benzylpiperidine-4-carboxylic acid ethyl ester

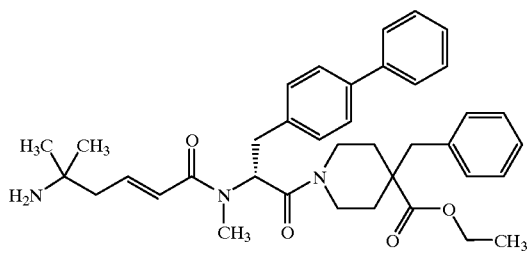

LC-MS: Rt=12.11 min, m/z: 610.4 (M+H)
HPLC: Rt=42.075 min (A1)
HPLC: Rt=44.383 min (B1).

Example 10

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid ethyl ester

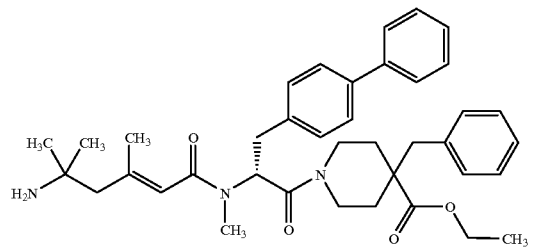

LC-MS: Rt=12.36 min, m/z: 624.4 (M+H)
HPLC: Rt=42.785 min (A1)
HPLC: Rt=45.148 min (B1).

Example 11

1-{(2R)-2-[N-((2E)-5-Amino-5-methylhex-2-enoyl)-N-methylamino]-3-(2-naphthyl)propionyl}-4-benzylpiperidine-4-carboxylic acid ethyl ester

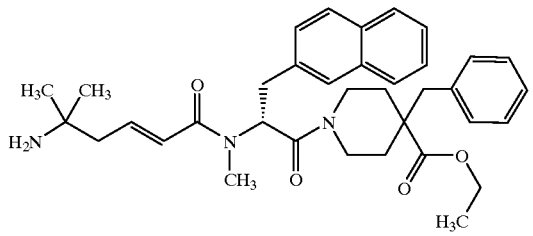

LC-MS: Rt=11.92 min, m/z: 584.4 (M+H)
HPLC: Rt=39.893 min (A1)
HPLC: Rt=42.046 min (B1).

Example 12

1-{(2R)-2-[N-((2E)-5-Amino-3,5-dimethylhex-2-enoyl)-N-methylamino]-3-(2-naphthyl)propionyl}-4-benzylpiperidine-4-carboxylic acid ethyl ester

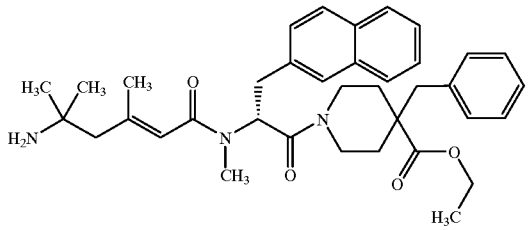

LC-MS: Rt=12.21 min, m/z: 598.2 (M+H)
HPLC: Rt=40.541 min (A1)
HPLC: Rt=42.780 min (B1).

Example 13

(3S)-1-[(2R)-2-((2E)-5-Amino-5-methylhex-2-enoylamino)-3-(1H-indol-3-yl)propionyl]-3-benzylpiperidine-3-carboxylic acid ethyl ester

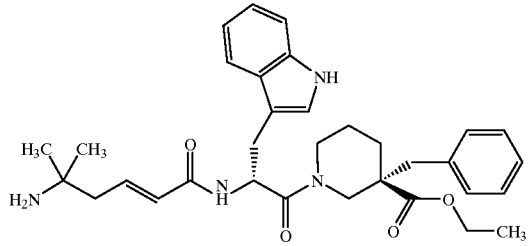

LC-MS: Rt=10.07 min, m/z: 559.4 (M+H)
HPLC: Rt=35.585 min (A1)
HPLC: Rt=37.441 min (B1).

Example 14

(3S)-1-[(2R)-2-((2E)-5-Amino-3,5-dimethylhex-2-enoylamino)-3-(1H-indol-3-yl)propionyl]-3-benzylpiperidine-3-carboxylic acid ethyl ester

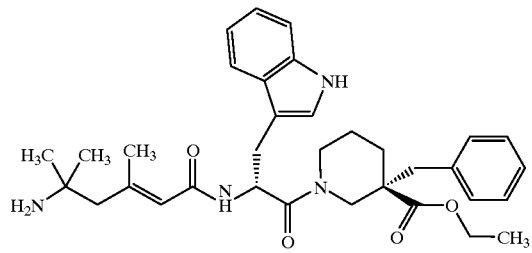

LC-MS: Rt=10.42 min, m/z: 573.2 (M+H)
HPLC: Rt=36.680 min (A1)
HPLC: Rt=38.563 min (B1).

Example 15

(3S)-1-[(2R)-2-(3-(Aminomethyl)benzoylamino)-3-(1H-indol-3-yl)propionyl]-3-benzylpiperidine-3-carboxylic acid ethyl ester

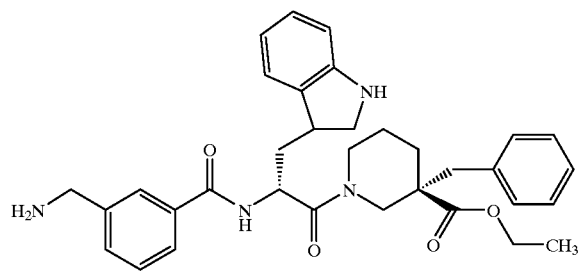

LC-MS: Rt=10.24 min, m/z: 567.4 (M+H)
HPLC: Rt=36.118 min (A1)
HPLC: Rt=38.052 min (B1).

Example 16

(2E)-5-Amino-5-methylhex-2-enoic acid N-{(1R)-2-[4-benzyl-4-(N',N'-dimethylhydrazinocarbonyl)piperidin-1-yl]-1-((2-naphthyl)methyl)-2-oxoethyl}-N-methylamide

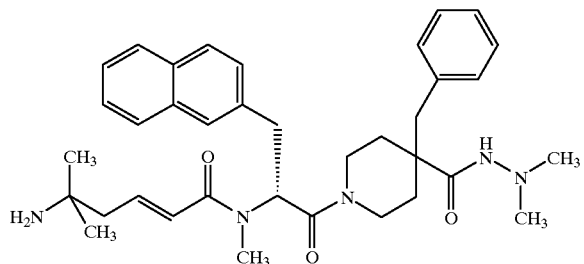

LC-MS: Rt=8.82 min, m/z: 598.4 (M+H)
HPLC: Rt=30.858 min (A1)
HPLC: Rt=31.198 min (B1).

Example 17

(2E)-5-Amino-5-methylhex-2-enoic acid N-[(1R)-2-[3-benzyl-3-(N',N'-dimethylhydrazinocarbonyl)-piperidin-1-yl]-1-((1H-indol-3-yl)methyl)-2-oxoethyl]amide

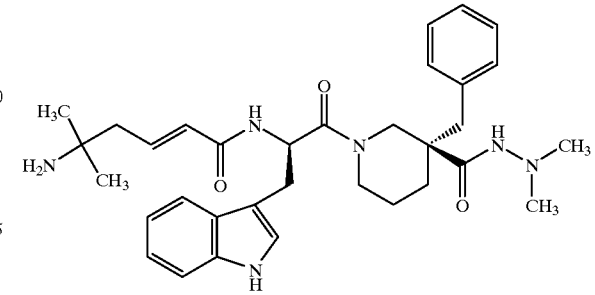

ESMS: m/z: 573.2 (M+H)$^+$.

Example 18

(2E)-5-Amino-5-methylhex-2-enoic acid N-{(1R)-2-[3-benzyl-3-(N',N'-dimethylhydrazinocarbonyl)-piperidin-1-yl]-1-((2-naphthyl)methyl)-2-oxoethyl}-N-methyl-amide

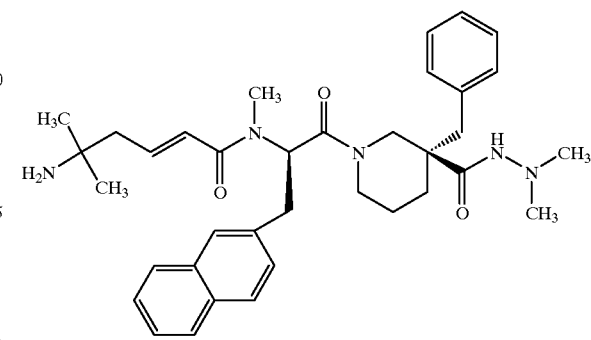

ESMS: m/z: 598.4 (M+H)$^+$.

Example 19

(2E)-5-Amino-5-methylhex-2-enoic acid {(1R)-2-[3-benzyl-3-(N',N'-dimethyl-hydrazinocarbonyl)piperidin-1-yl]-1-(benzyloxymethyl)-2-oxoethyl}amide

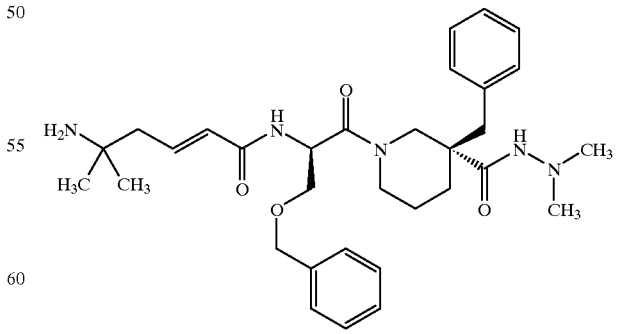

LC-MS: Rt=8.77 min; m/z: 564.2 (M+H)
HPLC: Rt=29.829 min (A1)
HPLC: Rt=29.250 min (B1).

Example 20

2-Amino-N-{2-[3-benzyl-3-(N',N'-dimethylhydrazinocarbonyl)piperidin-1-yl]-1-((2-naphthyl)methyl)-2-oxo-ethyl}-2-methyl-propionamide

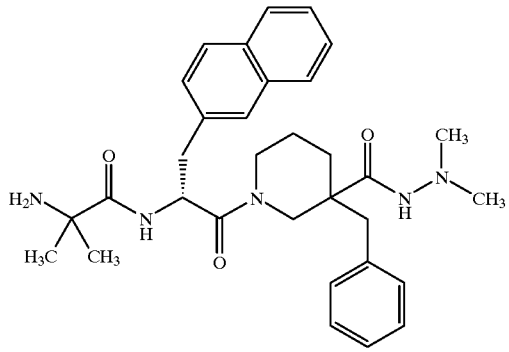

LC-MS: Rt=4.77 min; m/z: 544.4 (M+H)
HPLC: Rt=30.900/31.586 min (A1)
HPLC: Rt=30.188/30.727 min (B1).

Example 21

2-Amino-N-{(1R)-2-[3-benzyl-3-(N',N'-dimethylhydrazinocarbonyl)piperidin-1-y]-1-((biphenyl-4-yl)methyl)-2-oxoethyl}-2-methylpropionamide

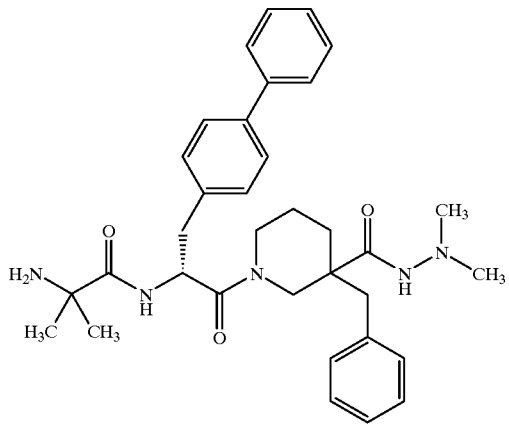

LC-MS: Rt=4.98 min; m/z: 570.4 (M+H)
HPLC: Rt=33.839/34.313 min (A1)
HPLC: Rt=33.297/33.640 min (B1).

Example 22

2-Amino-N-{(1R)-2-[3-benzyl-3-(N',N'-dimethylhydrazinocarbonyl)piperidin-1-yl]-1-((1H-indol-3-yl)methyl)-2-oxoethyl}-2-methylpropionamide

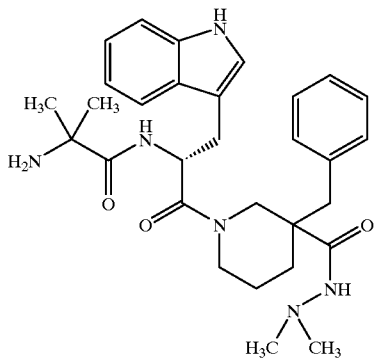

LC-MS: Rt=4.32 min; m/z: 533.4 (M+H)
HPLC: Rt=25.946/27.231 min (A1)
HPLC: Rt=25.822/26.685 (B1).

Example 23

2-Amino-N-{2-[3-benzyl-3-(N'-dimethylhydrazinocarbonyl)piperidin-1-yl]-1-(benzyloxymethyl)-2-oxoethyl}-2-methylpropionamide

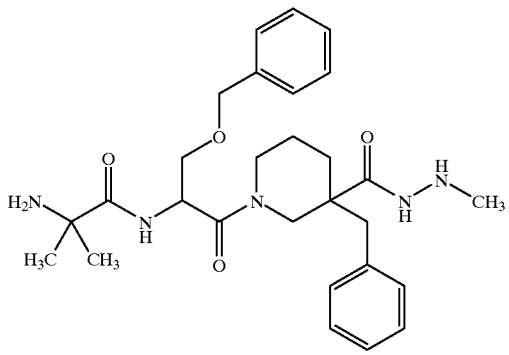

LC-MS: Rt=4.33/4.75 min; m/z: 510.4 (M+H)
HPLC: Rt=30.737/30.945 (A1)
HPLC: Rt=26.809/27.307 (B1).

Example 24

2-Amino-N-{(1R)-2-[3-benzyl-3-(N',N'-dimethylhydrazinocarbonyl)piperidin-1-yl]-1-(benzyloxymethyl)-2-oxoethyl}-2-methylpropionamide

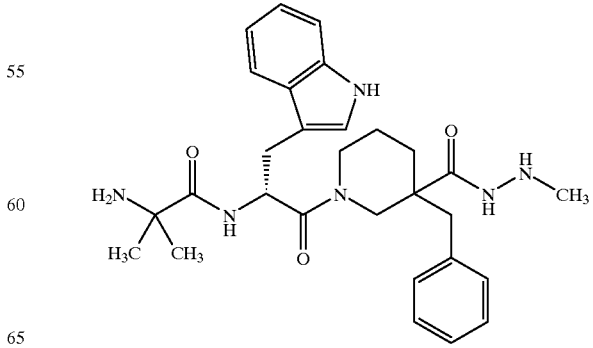

LC-MS: Rt=4.25/5.27 min; m/z: 519.4 (M+H)
HPLC: Rt=24.994 min (A1)
HPLC: Rt=25.742 min (B1).

Example 25

1-[(2R)-2-(2-Amino-2-methylpropionylamino)-3-(1-H-indol-3-yl)propionyl]-3-benzylpiperidine-3-carboxylic acid (pyrrolidin-1-yl)amide

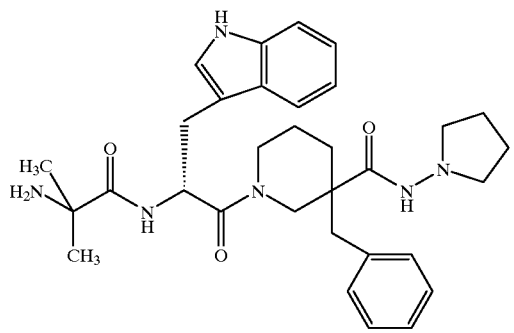

Mixture of Diastereomer

Diastereomer I:

LC-MS: Rt=4.40 min; m/z: 559.4 (M+H)
HPLC: Rt=26,04 min (A1)
HPLC: Rt=25,79 min (B1).
Diastereomer II:
HPLC: Rt=27,38 min (A1)

Example 26

2-Amino-N-{(1R)-2-[3-benzyl-3-(N,N',N'-trimethylhydrazinocarbonyl)piperidin-1-yl]-1-((1H-indol-3yl)-2-oxoethyl}-2-methylpropionamide

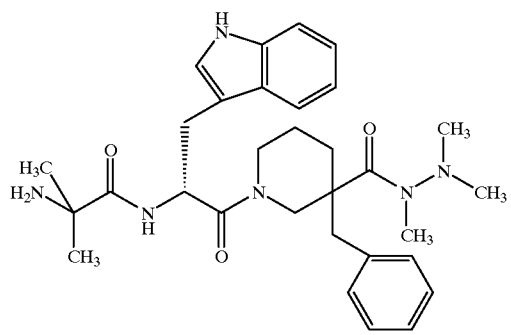

Mixture of Diastereomer

Diastereomer I:

LC-MS: Rt=5,07 min; m/z: 547,4 (M+H)
HPLC: Rt=32,16 min (A1).
Diastereomer II:
LC-MS: Rt=5,24 min; m/z: 547,4 (M+H)
HPLC: Rt=33,60 min (A1).

The compounds in examples 9–26 were prepared using the procedures in examples 1–6.

What is claimed is:

1. A compound of formula I

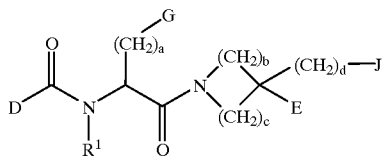

formula I wherein $R^1$ is hydrogen, or $C_{1-6}$-alkyl optionally substituted with one or more aryl or hetaryl;

a and d are independently of each other 0, 1, 2 or 3;

b and c are independently of each other 0, 1, 2, 3, 4 or 5, provided that b+c is 3, 4 or 5, D is

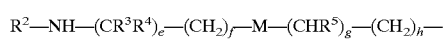

wherein $R^2$, $R^3$, $R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ may optionally form —(CH$_2$)$_i$—U—(CH$_2$)$_j$—, wherein i and j are independently 1 or 2 and U is —O—, —S— or a valence bond;

h and f are independently 0, 1, 2, or 3;

g and e are independently 0 or 1;

M is a valence bond, —CR$^6$=CR$^7$—, arylene, hetarylene, —O— or —S—;

$R^6$ and $R^7$ are independently hydrogen, or $C_{1-6}$-alkyl optionally substituted with one or more aryl or hetaryl;

G is —O—(CH$_2$)$_k$—R$^8$,

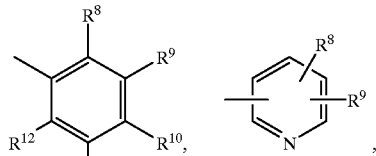

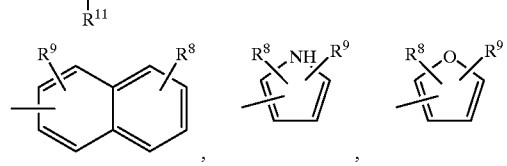

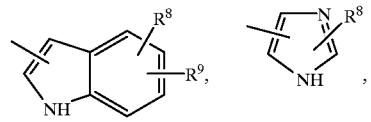

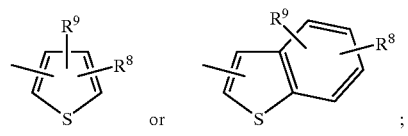

or ;

J is —O—(CH$_2$)$_l$—R$^{13}$,

-continued

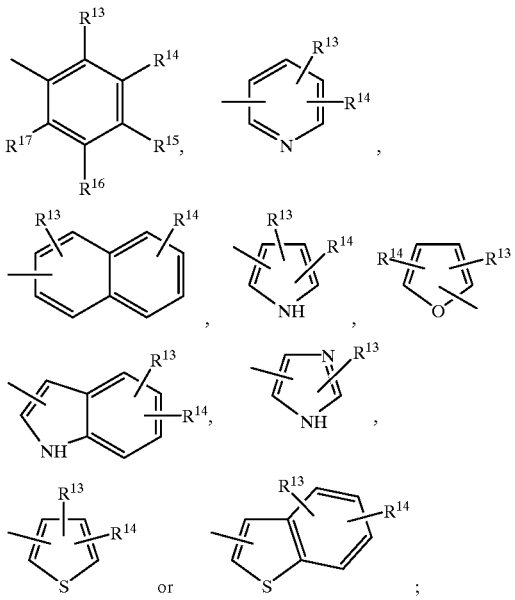

wherein $R^8$, $R^9$, $R^{10}$, $R^{11}$, $R^{12}$, $R^{13}$, $R^{14}$, $R^{15}$, $R^{16}$ and $R^{17}$ independently of each other are hydrogen, halogen, aryl, hetaryl, $C_{1-6}$-alkyl or $C_{1-6}$-alkoxy;

k and l are independently 0, 1 or 2;

E is —CONR$^{18}$R$^{19}$, —COOR$^{19}$, —(CH$_2$)$_m$—NR$^{18}$SO$_2$R$^{20}$, —(CH$_2$)$_m$—NR$^{18}$COR$^{20}$, —(CH$_2$)$_m$—OR$^{19}$, —(CH$_2$)$_m$—OCOR$^{20}$, —CH(R$^{18}$)R$^{19}$, —(CH$_2$)$_m$—NR$^{18}$—CS—NR$^{19}$R$^{21}$ or —(CH$_2$)$_m$—NR$^{18}$—CO—NR$^{19}$R$^{21}$; or

E is —CONR$^{22}$NR$^{23}$R$^{24}$, wherein R$^{22}$ is hydrogen, $C_{1-6}$-alkyl optionally substituted with one or more aryl or hetaryl, or aryl or hetaryl optionally substituted with one or more $C_{1-6}$-alkyl; R$^{23}$ is $C_{1-6}$-alkyl optionally substituted with one or more aryl or hetaryl, or $C_{1-7}$-acyl; and R$^{24}$ is hydrogen, $C_{1-6}$-alkyl optionally substituted with one or more aryl or hetaryl; or aryl or hetaryl optionally substituted with one or more $C_{1-6}$-alkyl; or R$^{22}$ and R$^{23}$ together with the nitrogen atoms to which they are attached may form a heterocyclic system optionally substituted with one or more $C_{1-6}$-alkyl, halogen, amino, hydroxyl, aryl or hetaryl; or R$^{22}$ and R$^{24}$ together with the nitrogen atoms to which they are attached may form a heterocyclic system optionally substituted with one or more $C_{1-6}$-alkyl, halogen, amino, hydroxyl, aryl or hetaryl; or R$^{23}$ and R$^{24}$ together with the nitrogen atom to which they are attached may form a heterocyclic system optionally substituted with one or more $C_{1-6}$-alkyl, halogen, amino, hydroxyl, aryl or hetaryl;

wherein m is 0, 1, 2 or 3,

R$^{18}$, R$^{19}$ and R$^{21}$ independently are hydrogen or $C_{1-6}$-alkyl optionally substituted with halogen, —N(R$^{25}$)R$^{26}$, wherein R$^{25}$ and R$^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl;

or R$^{19}$ is

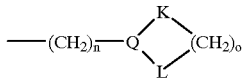

wherein
Q is —CH< or —N<,
K and L are independently —CH$_2$—, —CO—, —O—, —S—, —NR$^{27}$— or a valence bond,
where R$^{27}$ is hydrogen or $C_{1-6}$ alkyl;
n and o are independently 0, 1, 2, 3 or 4;
R$^{20}$ is $C_{1-6}$ alkyl, aryl or hetaryl;
or a pharmaceutically acceptable salt thereof;
with the proviso that if M is a valence bond then E is —CONR$^{22}$NR$^{23}$R$^{24}$.

2. The compound of claim 1 wherein R$^1$ is $C_{1-6}$-alkyl.
3. The compound of claim 1 wherein a is 1.
4. The compound of claim 1 wherein d is 1.
5. The compound of claim 1 wherein b+c is 4.
6. The compound of claim 1 wherein D is

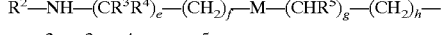

wherein R$^2$, R$^3$, R$^4$ and R$^5$ are independently hydrogen or $C_{1-6}$ alkyl optionally substituted with a halogen, amino, hydroxyl, aryl or hetaryl; or
R$^2$ and R$^3$ or R$^2$ and R$^4$ or R$^3$ and R$^4$ may optionally form —(CH$_2$)$_i$—U—(CH$_2$)$_j$—, wherein i and j are independently 1 or 2 and U is —O—, —S— or a valence bond;
h and f are independently 0, 1, 2, or 3;
g and e are independently 0 or 1;
M is —CR$^6$=CR$^7$—, arylene, hetarylene, —O— or —S—;
R$^6$ and R$^7$ are hydrogen, or $C_{1-6}$-alkyl.

7. The compound of claim 1 wherein D is

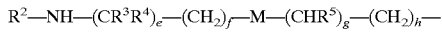

wherein R$^2$, R$^3$, R$^4$ and R$^5$ are independently hydrogen or $C_{1-6}$ alkyl optionally substituted with a halogen, amino, hydroxyl, aryl or hetaryl; or
R$^2$ and R$^3$ or R$^2$ and R$^4$ or R$^3$ and R$^4$ may optionally form —(CH$_2$)$_i$—U—(CH$_2$)$_j$—, wherein i and j are independently 1 or 2 and U is —O—, —S— or a valence bond;
h and f are independently 0, 1, 2, or 3;
g and e are independently 0 or 1;
M is a valence bond.

8. The compound of claim 1 wherein G is

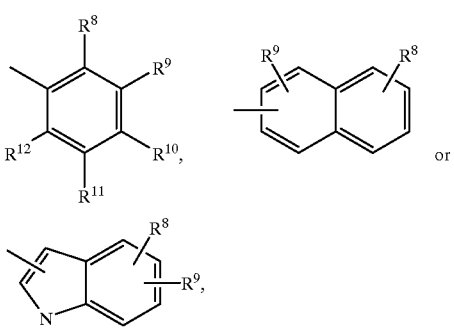

wherein $R^8$, $R^9$, $R^{10}$, $R^{11}$ and $R^{12}$ independently of each other are hydrogen, halogen, aryl, hetaryl, $C_{1-6}$-alkyl or $C_{1-6}$alkoxy; and k is 0, or 2.

9. The compound of claim 1 wherein J is

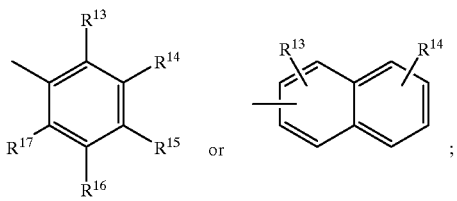

wherein $R^{13}$, $R^{14}$, $R^{15}$ $R^{16}$ and $R^{17}$ independently of each other are hydrogen, halogen, aryl, hetaryl, $C_{1-6}$-alkyl or $C_{1-6}$-alkoxy.

10. The compound of claim 1 wherein E is —$CONR^{18}R^{19}$, —$COOR^{19}$ or —$(CH_2)_m$—$OR^{19}$, wherein m is 0, 1, 2 or 3, $R^{18}$ and $R^{19}$ independently are hydrogen or $C_{1-6}$-alkyl optionally substituted by halogen, —$N(R^{25})R^{26}$ wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl.

11. The compound of claim 1 wherein E is —$CONR^{22}NR^{23}R^{24}$, wherein $R^{22}$ is hydrogen, $C_{1-6}$-alkyl optionally substituted with an aryl or hetaryl, or aryl or hetaryl optionally substituted with a $C_{1-6}$-alkyl; $R^{23}$ is $C_{1-6}$-alkyl optionally substituted with one or more aryl or hetaryl, or $C_{1-7}$-acyl; and $R^{24}$ is hydrogen, $C_{1-6}$-alkyl optionally substituted with an aryl or hetaryl; or aryl or hetaryl optionally substituted with a $C_{1-6}$-alkyl; or $R^{22}$ and $R^{23}$ together with the nitrogen atoms to which they are attached may form a heterocyclic system optionally substituted with a $C_{1-6}$-alkyl, halogen, amino, hydroxyl, aryl or hetaryl; or $R^{22}$ and $R^{24}$ together with the nitrogen atoms to which they are attached may form a heterocyclic system optionally substituted with a $C_{1-6}$-alkyl, halogen, amino, hydroxyl, aryl or hetaryl; or $R^{23}$ and $R^{24}$ together with the nitrogen atom to which they are attached may form a heterocyclic system optionally substituted with a $C_{1-6}$-alkyl, halogen, amino, hydroxyl, aryl or hetaryl.

12. The compound according to claim 1 selected from

1-{(2R)-2-[N-((2E)-5-Amino-5-methylhex-2-enoyl)-N-methylamino]-3-(2-naphthyl)propionyl}-4-benzylpiperidine-4-carboxylic acid methylamide

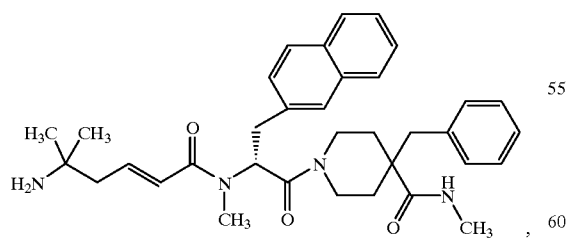

1-{(1R)-2-[N-((2E)-5-Amino-3,5-dimethylhex-2-enoyl)-N-methylamino]-3-(2-naphthyl)propionyl}-4-benzylpiperidine-4-carboxylic acid methylamide

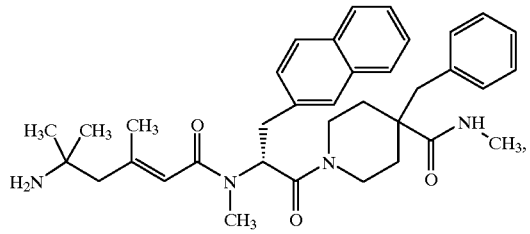

1-{(2R)-2-[N-((2E)-5-Amino-5-methylhex-2-enoyl)-N-methylamino]-3-(biphenyl-4-yl)propionyl}4-benzylpiperidine-4-carboxylic acid methylamide

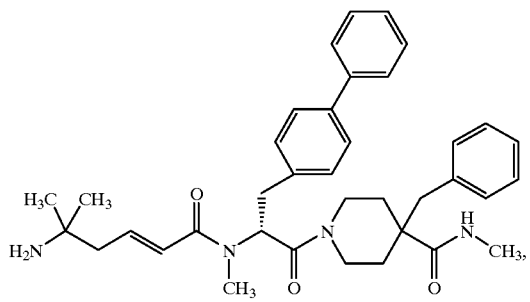

1-{(2R)-2-[N-((2E)-5-Amino-3,5-dimethylhex-2-enoyl)-N-methylamino]-3-(biphenyl-4-yl)propionyl}4-benzylpiperidine-4-carboxylic acid methylamide

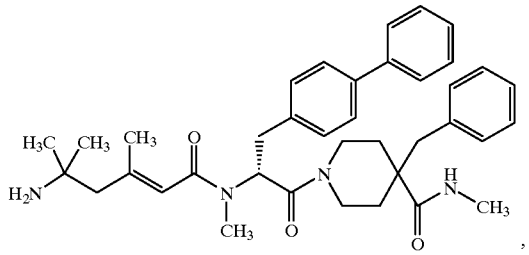

1-((2R)-2-{N-[(2E)4-(1-Aminocyclobutyl)but-2-enoyl]-N-methylamino}-3-(biphenyl-4-yl)propionyl)4-benzylpiperidine-4-carboxylic acid methylamide

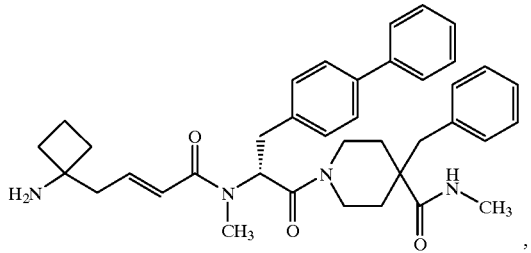

2-Amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide

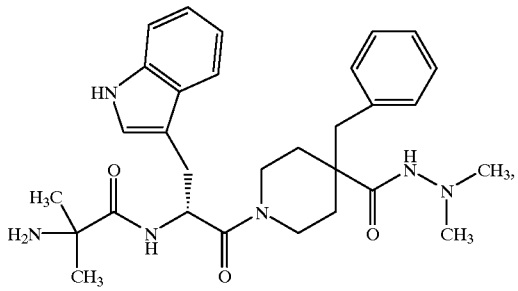

2-Amino-N-{(1R)-2-[(3R)-3-benzyl-3-(N',N'-dimethyl-hydrazinocarbonyl)-piperidin-1-yl]-1-benzyloxymethyl-2-oxo-ethyl}-2-methyl-propionamide

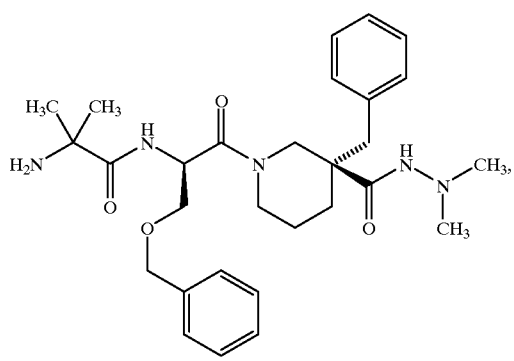

2-Amino-N-[(1R)-2-[(3R)-3-benzyl-3-(N'N'-dimethylhydrazinocarbonyl)-piperidin-1-yl]-1-((1H-indol-3-yl)methyl)-2-oxoethyl]-2-methylpropionamide

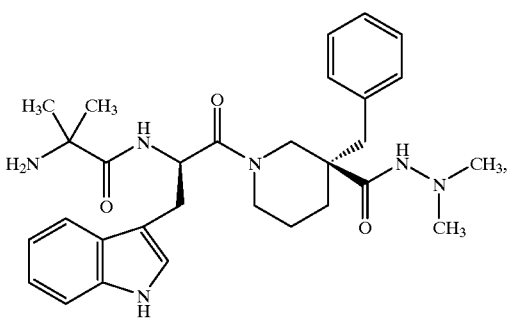

1-{(2R)-2-[N-((2E)-5-Amino-5-methylhex-2-enoyl)-N-methylamino]-3-(biphenyl-4-yl)propionyl}-4-benzylpiperidine-4-carboxylic acid ethyl ester

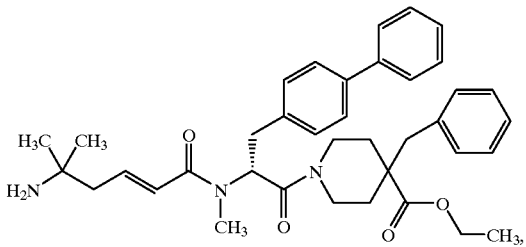

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid ethyl ester

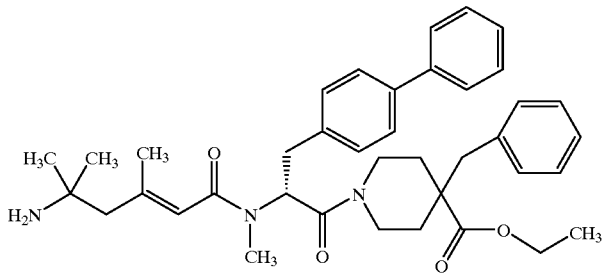

1-{(2R)-2-[N-((2E)-5-Amino-5-methylhex-2-enoyl)-N-methylamino]-3-(2-naphthyl)propionyl}-4-benzylpiperidine-4-carboxylic acid ethyl ester

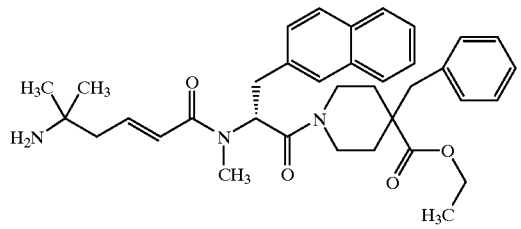

1-{(2R)-2-[N-((2E)-5-Amino-3,5-dimethylhex-2-enoyl)-N-methylamino]-3-(2-naphthyl)propionyl}-4-benzylpiperidine-4-carboxylic acid ethyl ester

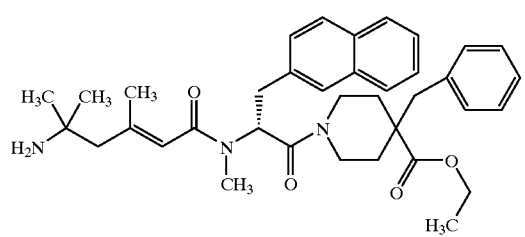

(3S)-1-[(2R)-2-((2E)-5-Amino-5-methylhex-2-enoylamino)-3-(1H-indol-3-yl)propionyl]-3-benzylpiperidine-3-carboxylic acid ethyl ester

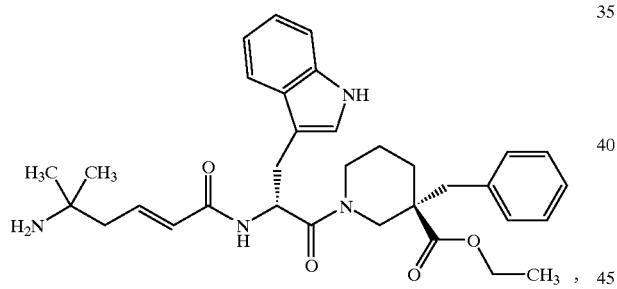

(3S)-1-[(2R)-2-((2E)-5-Amino-3,5-dimethylhex-2-enoylamino)-3-(1H-indol-3-yl)propionyl]-3-benzylpiperidine-3-carboxylic acid ethyl ester

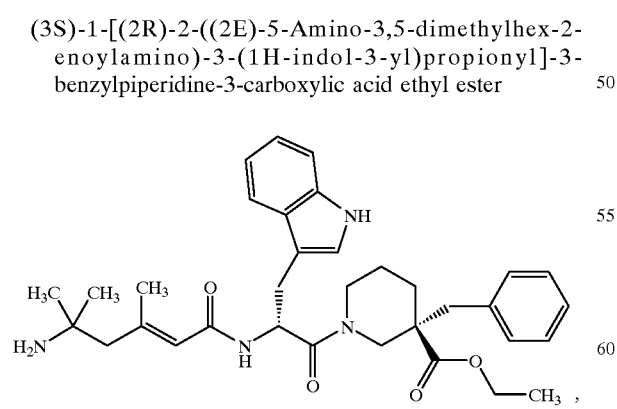

(3S)-1-[(2R)-2-(3-(Aminomethyl)benzoylamino)-3-(1H-indol-3-yl)propionyl]-3-benzylpiperidine-3-carboxylic acid ethyl ester

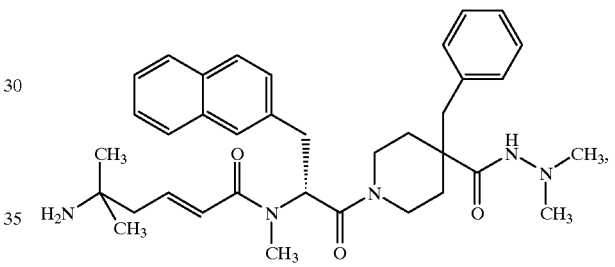

(2E)-5-Amino-5-methylhex-2-enoic acid N-{(1R)-2-[4-benzyl-4-(N',N'-dimethylhydrazinocarbonyl)piperidin-1-yl]-1-((2-naphthyl)methyl)-2-oxoethyl}-N-methylamide

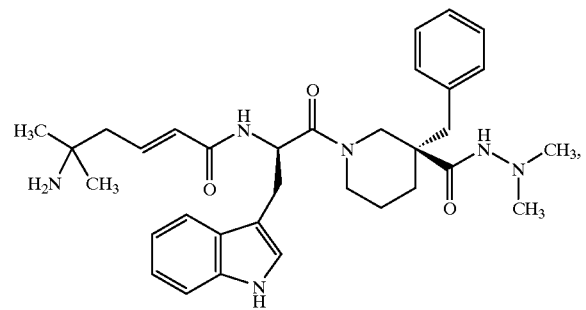

(2E)-5-Amino-5-methylhex-2-enoic acid N-[(1R)-2-[3-benzyl-3-(N',N'-dimethylhydrazinocarbonyl)-piperidin-1-yl]-1-((1H-indol-3-yl)methyl)-2-oxoethyl]amide (2E)-5-Amino-5-methylhex-2-enoic acid N-{(1R)-2-[3-benzyl-3-(N',N'-dimethylhydrazinocarbonyl)-piperidin-1-yl]-1-((2-naphthyl)methyl)-2-oxoethyl}-N-methyl-amide

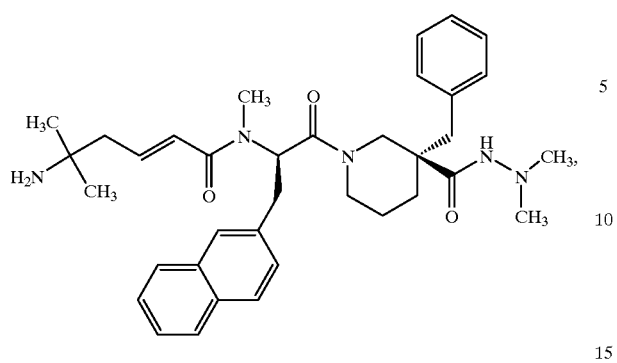

(2E)-5-Amino-5-methylhex-2-enoic acid {(1R)-2-[3-benzyl-3-(N',N'-dimethyl-hydrazinocarbonyl)piperidin-1-yl]-1-(benzyloxymethyl)-2-oxoethyl}amide

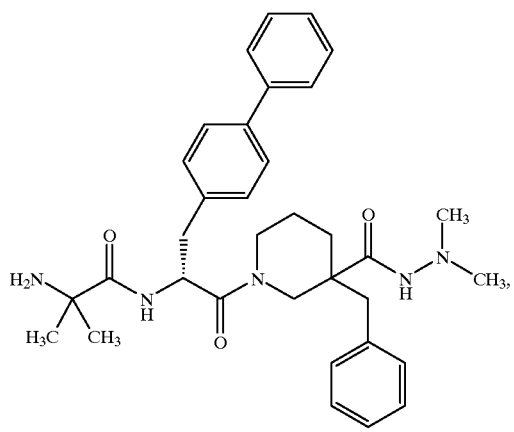

2-Amino-N-{(1R)-2-[3-benzyl-3-(N',N'-dimethylhydrazinocarbonyl)piperidin-1-yl]-1-((1H-indol-3-yl)methyl)-2-oxoethyl}-2-methylpropionamide

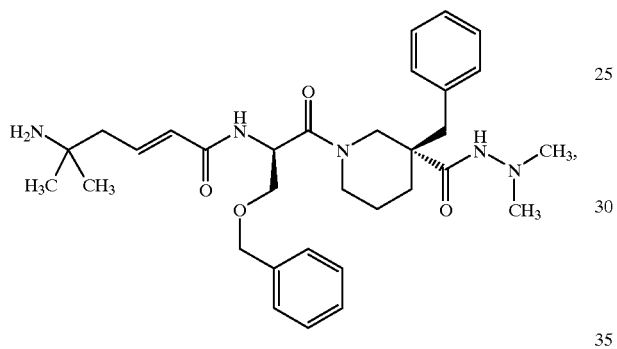

2-Amino-N-{2-[3-benzyl-3-(N',N'-dimethylhydrazinocarbonyl)piperidin-1-yl]-1-((2-naphthyl)methyl)-2-oxo-ethyl}-2-methyl-propionamide

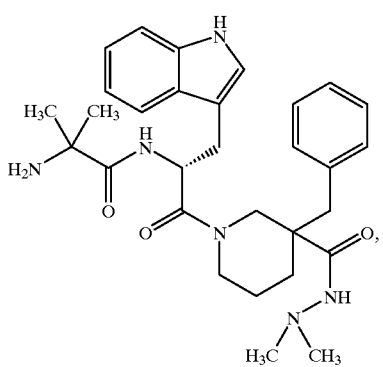

2-Amino-N-{2-[3-benzyl-3-(N',N'-dimethylhydrazinocarbonyl)piperidin-1-yl]-1-(benzyloxymethyl)-2-oxoethyl}-2-methylpropionamide

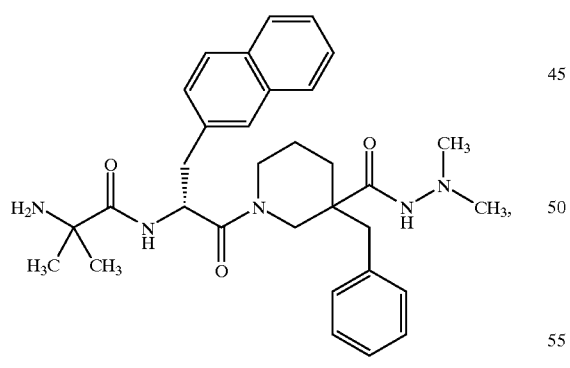

2-Amino-N-{(1R)-2-[3-benzyl-3-(N',N'-dimethylhydrazinocarbonyl)piperidin-1-yl]-1-((biphenyl-4-yl)methyl)-2-oxoethyl}-2-methylpropionamide

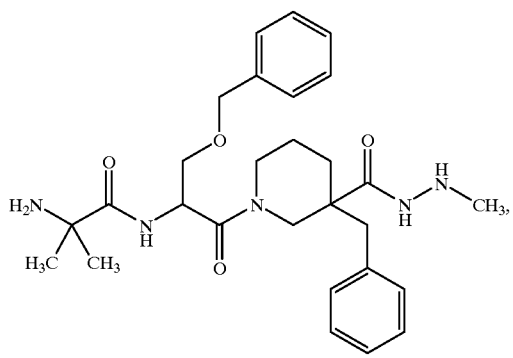

2-Amino-N-{(1R-2-[3-benzyl-3-(N',N'-dimethylhydrazinocarbonyl)piperidin-1-yl]-1-(benzyloxymethyl)-2-oxoethyl}-2-methylpropionamide

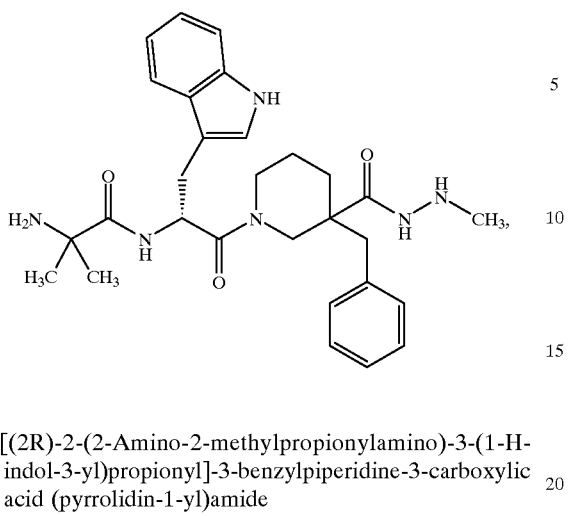

1-[(2R)-2-(2-Amino-2-methylpropionylamino)-3-(1-H-indol-3-yl)propionyl]-3-benzylpiperidine-3-carboxylic acid (pyrrolidin-1-yl)amide

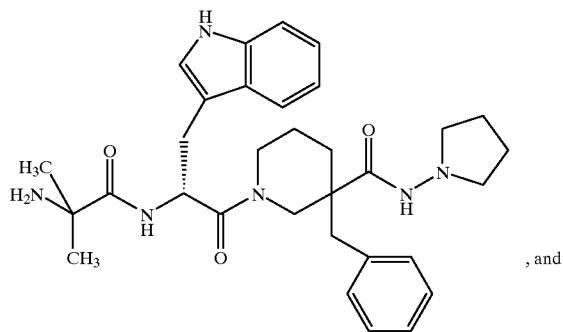, and

2 A m i n o - N - {(1R) - 2 - [3 b e n z y l - 3 - (N,N',N'-trimethylhydrazinocarbonyl)piperidin-1-yl]-1-((1H-indol-3-yl)methyl)-2-oxoethyl}-2-methylpropionamide

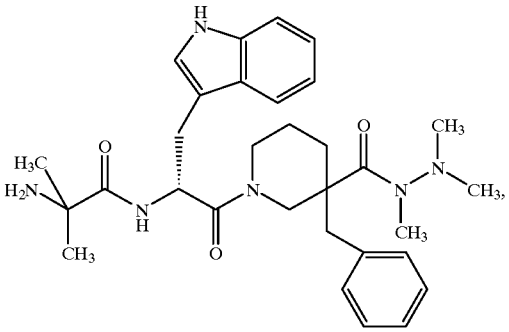

and pharmaceutically acceptable salts thereof.

13. A pharmaceutical composition comprising, as an active ingredient, an effective amount of a compound of claim 1 together with a pharmaceutically acceptable carrier or diluent.

14. A method of stimulating the release of growth hormone from the pituitary of a mammal, the method comprising administering to the mammal an effective amount of a compound of claim 1 or a composition of claim 13.

* * * * *